(12) United States Patent
Yi et al.

(10) Patent No.: US 9,907,528 B2
(45) Date of Patent: Mar. 6, 2018

(54) X-RAY IMAGING APPARATUS, IMAGE PROCESSING APPARATUS AND IMAGE PROCESSING METHOD

(71) Applicant: SAMSUNG ELECTRONICS CO., LTD., Suwon-si (KR)

(72) Inventors: Jae Mock Yi, Hwaseong-si (KR); Dong-Goo Kang, Hwaseong-si (KR); Young Hun Sung, Hwaseong-si (KR); Jae Hak Lee, Yongin-si (KR); Ji Young Choi, Suwon-si (KR); Seok Min Han, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 129 days.

(21) Appl. No.: 14/868,887

(22) Filed: Sep. 29, 2015

(65) Prior Publication Data

US 2016/0213344 A1 Jul. 28, 2016

(30) Foreign Application Priority Data

Jan. 22, 2015 (KR) .................. 10-2015-0010423

(51) Int. Cl.
*G06K 9/00* (2006.01)
*A61B 6/00* (2006.01)
(Continued)

(52) U.S. Cl.
CPC .......... *A61B 6/5282* (2013.01); *A61B 6/4241* (2013.01); *A61B 6/482* (2013.01);
(Continued)

(58) Field of Classification Search
CPC ........... G06T 5/00; G06T 5/001; G06T 5/002; G06T 2207/10116; A61B 6/5258; A61B 6/5282; A61B 6/5294; G01N 23/00; G01N 23/02; G01N 23/04; G01N 23/06; G01N 23/063; G01N 23/08; G01N 23/083; G03B 42/02
USPC ................ 382/128, 130–132, 172, 254, 275; 378/5–8, 51–54, 70, 86–90, 98.4, 98.9, 378/98.11, 98.12
See application file for complete search history.

(56) References Cited

U.S. PATENT DOCUMENTS 6,922,462 B2 * 7/2005 Acharya ............... G06T 7/0012
378/98.11
6,987,833 B2 * 1/2006 Du ......................... A61B 6/032
378/5

(Continued)

FOREIGN PATENT DOCUMENTS

KR 10-2011-0105986 A 9/2011

*Primary Examiner* — Eric Rush
(74) *Attorney, Agent, or Firm* — Sughrue Mion, PLLC

(57) ABSTRACT

An X-ray imaging apparatus may include an image acquirer configured to acquire a plurality of X-ray images of an object in different energy bands; and an image processor configured to perform scattering correction on the plurality of X-ray images to remove X-ray scattering from the plurality of X-ray images, perform material separation on the plurality of X-ray images on which the scattering correction has been performed to acquire material information of at least one material included in the object, and repeatedly perform the scattering correction and the material separation depending on whether a predetermined condition is satisfied.

33 Claims, 25 Drawing Sheets

(51) Int. Cl.
*G06T 5/00* (2006.01)
*G01N 23/083* (2018.01)
*G01N 23/06* (2018.01)

(52) U.S. Cl.
CPC ......... *A61B 6/5235* (2013.01); *G01N 23/063* (2013.01); *G01N 23/083* (2013.01); *G06T 5/00* (2013.01); *A61B 6/463* (2013.01); *G06T 2207/10116* (2013.01)

(56) References Cited

U.S. PATENT DOCUMENTS

| | | | | |
|---|---|---|---|---|
| 8,054,940 B2* | 11/2011 | Honda | ................... | G06T 7/0012 |
| | | | | 382/132 |
| 8,442,289 B2* | 5/2013 | Kadomura | .............. | G06T 7/174 |
| | | | | 382/132 |
| 9,047,397 B1* | 6/2015 | Temple | ................... | G01N 23/04 |
| 2005/0163283 A1* | 7/2005 | Bruder | ................... | A61B 6/032 |
| | | | | 378/98.11 |
| 2009/0122953 A1* | 5/2009 | Imai | ....................... | A61B 6/032 |
| | | | | 382/131 |
| 2009/0304249 A1 | 12/2009 | Wu | | |
| 2009/0323896 A1* | 12/2009 | Kitamura | ............. | A61B 6/4291 |
| | | | | 378/98.11 |
| 2010/0027867 A1* | 2/2010 | Bernhardt | ................ | A61B 6/00 |
| | | | | 382/132 |
| 2010/0046696 A1* | 2/2010 | Maltz | .................... | G06T 11/005 |
| | | | | 378/7 |
| 2012/0106816 A1 | 5/2012 | Bernard De Man et al. | | |
| 2012/0170826 A1 | 7/2012 | Jang et al. | | |
| 2013/0101089 A1* | 4/2013 | Cho | .......................... | A61B 6/463 |
| | | | | 378/62 |
| 2013/0142412 A1* | 6/2013 | Oh | ........................... | G06T 5/50 |
| | | | | 382/132 |
| 2014/0185901 A1* | 7/2014 | Edic | ...................... | G06T 11/003 |
| | | | | 382/132 |
| 2014/0348440 A1* | 11/2014 | Bergner | ................. | G06T 5/00 |
| | | | | 382/254 |
| 2016/0140720 A1* | 5/2016 | Naito | ................... | G06T 7/0075 |
| | | | | 382/132 |

* cited by examiner

FIG.13

| Dose(mGy) | 0.6 | 0.9 | 1.2 | 1.5 |
|---|---|---|---|---|
| CASE 1 | 1.86 | 2.24 | 2.46 | 2.86 |
| CASE 2 | 2.23 | 2.42 | 4.16 | 5.40 |
| CASE 3 | 4.45 | 5.58 | 6.30 | 7.46 |

X-RAY IMAGING APPARATUS, IMAGE PROCESSING APPARATUS AND IMAGE PROCESSING METHOD

CROSS-REFERENCE TO RELATED APPLICATION

This application claims priority from Korean Patent Application No. 10-2015-0010423, filed on Jan. 22, 2015, in the Korean Intellectual Property Office, the disclosure of which is incorporated herein in its entirety by reference.

BACKGROUND

1. Field

Apparatuses and methods consistent with exemplary embodiments relate to an X-ray imaging apparatus that separates a material using a multi-energy X-ray image, and an image processing apparatus, and an image processing method.

2. Description of the Related Art

An X-ray imaging apparatus is an apparatus that irradiates an object with X-rays and detects the X-rays transmitted through the object to image the internal structure of the object. Based on X-ray attenuation or absorption depending on characteristics of a material constituting the object, it is possible to image the internal structure of the object from the intensity of the X-ray transmitted through the object. However, materials having similar X-ray attenuation characteristics are difficult to be distinguished from each other in an X-ray image, and in a case of an X-ray projection image, materials overlapped with each other among the constituent materials of the object are difficult to be distinguished from each other.

SUMMARY

One or more exemplary embodiments provide an X-ray imaging apparatus that improves the accuracy of material separation of an object and scattering correction using a multi-energy image, an image processing apparatus, and a method for the same.

Additional aspects of the disclosure will be set forth in part in the description which follows and, in part, will be obvious from the description, or may be learned by practice of the exemplary embodiments.

According to an aspect of an exemplary embodiment, provided is an X-ray imaging apparatus including: an image acquirer configured to acquire a plurality of X-ray images of an object in different energy bands; and an image processor configured to perform scattering correction on the plurality of X-ray images to remove X-ray scattering from the plurality of X-ray images, perform material separation on the plurality of X-ray images on which the scattering correction has been performed to acquire material information of at least one material included in the object, and repeatedly perform the scattering correction and the material separation depending on whether a predetermined condition is satisfied.

When the predetermined condition is not satisfied, the image processor may be configured to repeatedly perform the scattering correction on the plurality of X-ray images by using the acquired material information, and repeatedly perform the material separation on the plurality of X-ray images on which the scattering correction has been performed.

When the predetermined condition is not satisfied, the image processor may be configured to estimate the X-ray scattering in the plurality of X-ray images by using the material information.

The image processor may be configured to perform the scattering correction by removing the estimated X-ray scattering from the plurality of X-ray images.

The material information may include a thickness of a material of the object in a field of view (FOV) of the plurality of X-ray images.

The predetermined condition may include whether a difference between X-ray intensity calculated based on the acquired material information and measured X-ray intensity is within a predetermined error range.

The predetermined condition may include whether a cost function defined by using the acquired material information is minimized.

The X-ray imaging apparatus may further include a display configured to provide the acquired material information to a user.

The display may be configured to display a material separation image generated by using the acquired material information.

The display may be configured to display an image obtained by combining the acquired material information and a highlighted material image, the highlighted material image being generated by applying weighted subtraction to the plurality of X-ray images.

The X-ray imaging apparatus may further include an input device configured to receive a selection of at least one from among a highlighted material image generated by applying weighted subtraction to the plurality of X-ray images and a material separation image generated by performing the material separation.

The X-ray imaging apparatus may further include a controller configured to select at least one from among a highlighted material image generated by applying weighted subtraction to the plurality of X-ray images and a material separation image generated by performing the material separation, based on imaging parameters of the plurality of X-ray images.

According to an aspect of an exemplary embodiment, provided is an X-ray imaging apparatus including: an image acquirer configured to acquire a plurality of X-ray images of an object in different energy bands; and an image processor configured to perform material separation on the plurality of X-ray images to acquire material information of at least one material included in the object, repeatedly perform scattering correction by using the acquired material information to remove X-ray scattering from the plurality of X-ray images and the material separation on the plurality of X-ray images on which the scattering correction has been performed, depending on whether a predetermined condition is satisfied.

When the predetermined condition is not satisfied, the image processor may be configured to repeatedly perform the scattering correction on the plurality of X-ray images by using the acquired material information, and repeatedly perform the material separation on the plurality of X-ray images on which the scattering correction has been performed.

The image processor may be configured to perform a first material separation without performing the scattering correction or after performing the scattering correction by using an initial scattering estimation value.

The X-ray imaging apparatus may further include a display configured to provide the acquired material information to a user.

According to an aspect of an exemplary embodiment, provided is an image processing apparatus including: a communicator configured to receive a plurality of X-ray images of an object in different energy bands; and an image processor configured to perform scattering correction on the plurality of X-ray images to remove X-ray scattering from the plurality of X-ray images, perform material separation on the plurality of X-ray images on which the scattering correction has been performed to acquire material information of at least one material included in the object, and repeatedly perform the scattering correction and the material separation depending on whether a predetermined condition is satisfied.

When the predetermined condition is not satisfied, the image processor may be configured to repeatedly perform the scattering correction on the plurality of X-ray images by using the acquired material information, and repeatedly perform the material separation on the plurality of X-ray images on which the scattering correction has been performed.

When the predetermined condition is not satisfied, the image processor may be configured to estimate the X-ray scattering in the plurality of X-ray images by using the material information, and perform the scattering correction by removing the estimated X-ray scattering from the plurality of X-ray images.

The material information may include a thickness of a material of the object in a field of view (FOV) of the plurality of X-ray images.

The image processing apparatus may further include an input device configured to receive a selection of at least one from among a highlighted material image generated by applying weighted subtraction to the plurality of X-ray images and a material separation image generated by performing the material separation.

The image processing apparatus may further include a display configured to provide the acquired material information to a user.

According to an aspect of an exemplary embodiment, provided is an image processing apparatus including: a communicator configured to receive a plurality of X-ray images of an object in different energy bands; an image processor configured to perform material separation on the plurality of X-ray images to acquire material information of at least one material included in the object, and repeatedly perform scattering correction by using the acquired material information to remove X-ray scattering from the plurality of X-ray images and the material separation on the plurality of X-ray images on which the scattering correction has been performed, depending on whether a predetermined condition is satisfied; and a display configured to provide the acquired material information to a user.

The image processor may be configured to repeatedly perform the scattering correction on the plurality of X-ray images by using the acquired material information and perform the material separation on the plurality of X-ray images on which the scattering correction has been performed when the predetermined condition is not satisfied.

The image processor may be configured to perform a first material separation without performing the scattering correction or after performing the scattering correction by using an initial scattering estimation value.

The predetermined condition may include whether a difference between X-ray intensity calculated based on the acquired material information and measured X-ray intensity is within a predetermined error range.

According to an aspect of an exemplary embodiment, provided is an image processing method including: performing scattering correction on a plurality of X-ray images of an object in different energy bands to remove X-ray scattering from the plurality of X-ray images; performing material separation on the plurality of X-ray images on which the scattering correction has been performed to acquire material information of at least one material included in the object; and repeatedly performing the scattering correction and the material separation depending on whether a predetermined condition is satisfied.

The repeatedly performing may include, when the predetermined condition is not satisfied, repeatedly performing the scattering correction on the plurality of X-ray images by using the acquired material information, and repeatedly performing the material separation on the plurality of X-ray images on which the scattering correction has been performed.

The image processing method may further include providing the acquired material information to a user when the predetermined condition is satisfied.

According to an aspect of an exemplary embodiment, provided is an image processing method including: performing material separation on a plurality of X-ray images of an object in different energy bands to acquire material information of at least one material included in the object; and repeatedly performing scattering correction by using the acquired material information to remove X-ray scattering from the plurality of X-ray images, and the material separation by using the plurality of X-ray images on which the scattering correction has been performed, depending on whether a predetermined condition is satisfied.

The repeatedly performing may include, when the predetermined condition is not satisfied, repeatedly performing the scattering correction on the plurality of X-ray images by using the acquired material information, and repeatedly performing the material separation on the plurality of X-ray images on which the scattering correction has been performed.

The display may be configured to display at least one of the highlighted material image, the material separation image, and an image obtained by combining the highlighted material image and the material separation image, according to the selection received by the input device.

The display may be configured to display at least one from among the highlighted material image, the material separation image, and an image obtained by combining the highlighted material image and the material separation image, according to selection by the controller.

BRIEF DESCRIPTION OF THE DRAWINGS

The above and/or other aspects will become more apparent by describing certain exemplary embodiments with reference to the accompanying drawings in which:

FIGS. 13 to 17 are views illustrating simulation results of an X-ray imaging apparatus according to an exemplary embodiment;

DETAILED DESCRIPTION

Figure 1:
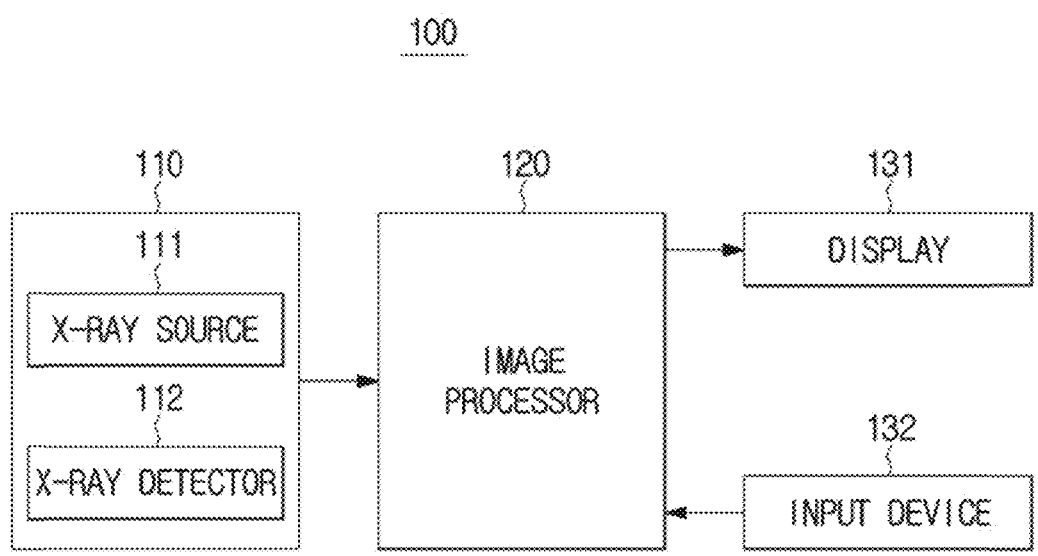
FIG. 1 is a control block diagram illustrating an X-ray imaging apparatus according to an exemplary embodiment.

Certain exemplary embodiments are described in greater detail below with reference to the accompanying drawings, wherein like reference numerals refer to like elements throughout. In this regard, the exemplary embodiments may have different forms and should not be construed as being limited to the descriptions set forth herein. Accordingly, the exemplary embodiments are merely described below, by referring to the figures, to explain aspects of the present description. Sizes of elements in the drawings may be exaggerated for convenience of explanation. In other words, since sizes and thicknesses of components in the drawings are arbitrarily illustrated for convenience of explanation, the following exemplary embodiments are not limited thereto.

Hereinafter, an X-ray imaging apparatus, an image processing apparatus, and a method for the same according to exemplary embodiments will be described in detail with reference to the accompanying drawings.

FIG. 1 is a control block diagram illustrating an X-ray imaging apparatus according to an exemplary embodiment.

Referring to FIG. 1, an X-ray imaging apparatus 100 according to an exemplary embodiment includes an image acquirer 110 that acquires a multi-energy X-ray image of an object, an image processor 120 that performs material separation and scattering correction by using the multi-energy X-ray image, a display 131 that provides results of material separation to a user, and an input device 132 that receives input control commands on operations of the image acquirer 110, the image processor 120, or the display 131 from the user.

The image acquirer 110 includes an X-ray source 111 that generates X-rays to irradiate an object with the generated X-rays, and an X-ray detector 112 that detects the X-rays transmitted through the object. In order for the image acquirer 110 to acquire the multi-energy X-ray image of the object, the X-ray source 111 may respectively generate X-rays of mutually different energy bands to irradiate generated X-rays. Alternatively, the X-ray source 111 may generate X-rays of a single energy band including all of the individual energy bands to irradiate the generated X-rays, and the X-ray detector may detect the irradiated X-rays to separate the detected X-rays for each energy band.

The multi-energy X-ray image may be used to indicate the inclusion of all of the individual X-ray images acquired from the mutually different energy bands. The number of the multi-energy X-ray images acquired by the image acquirer 110 may be two or three or more. In other words, the image acquirer 110 may acquire the multi-energy X-ray images from a first energy X-ray image acquired from a first energy band to an n-th energy X-ray image (n being an integer of two or greater) acquired from an n-th energy band. Here, n may be determined according to the number of materials desired to be separated.

The image processor 120 may quantitatively separate materials by using the multi-energy X-ray images. Here, the separated materials contain materials shown in the X-ray image. The separated material may be a material constituting the object, but is not limited thereto. For example, a tool used for diagnosis or surgical procedure inside or outside the object may be a separation target, and any material may be the separation target regardless of the material constituting the object, as long as the separation target is included in a field of view (FOV).

Since a scattering effect may be included in the multi-energy X-ray image, the corresponding material may be more accurately separated by performing scattering correction. To this end, the image processor 120 may improve the accuracy of material separation and scattering correction by performing material separation and scattering correction in a cyclic iterative manner. This will be described in detail later.

The display 131 may display and provide results of material separation of the image processor 120 to a user. The display 131 may display each of material separation images, emphasize one of the material separation images than the rest of the material separation images, and display the separated material in a highlighted material image acquired by applying weighted subtraction to the multi-energy X-ray image, or display quantitative information of the separated material together with the material separation image or the highlighted material image. There is no limitation in a method of displaying the results of material separation by the display 131 of the X-ray imaging apparatus, 100 and the results of material separation may be provided to the user according to various methods other than the above-described method.

Hereinafter, operations of the individual components of the X-ray imaging apparatus 100 will be described.

Figure 2:
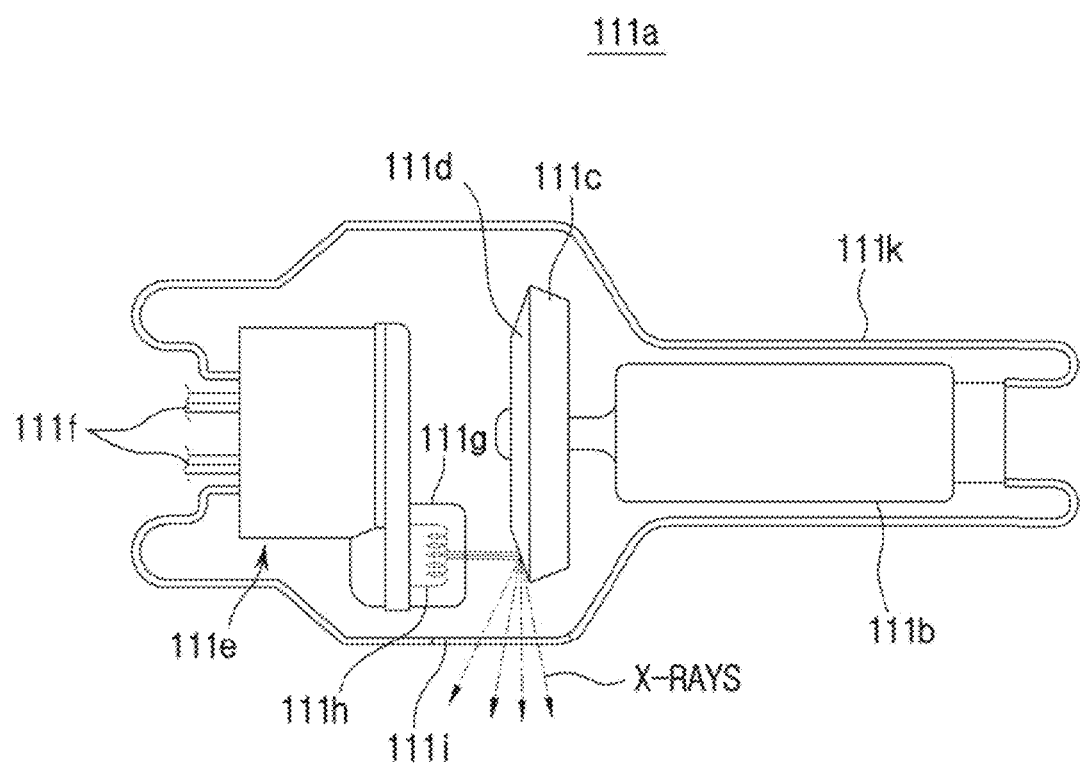
FIG. 2 is a diagram illustrating an internal structure of an X-ray tube.
Figure 3A:
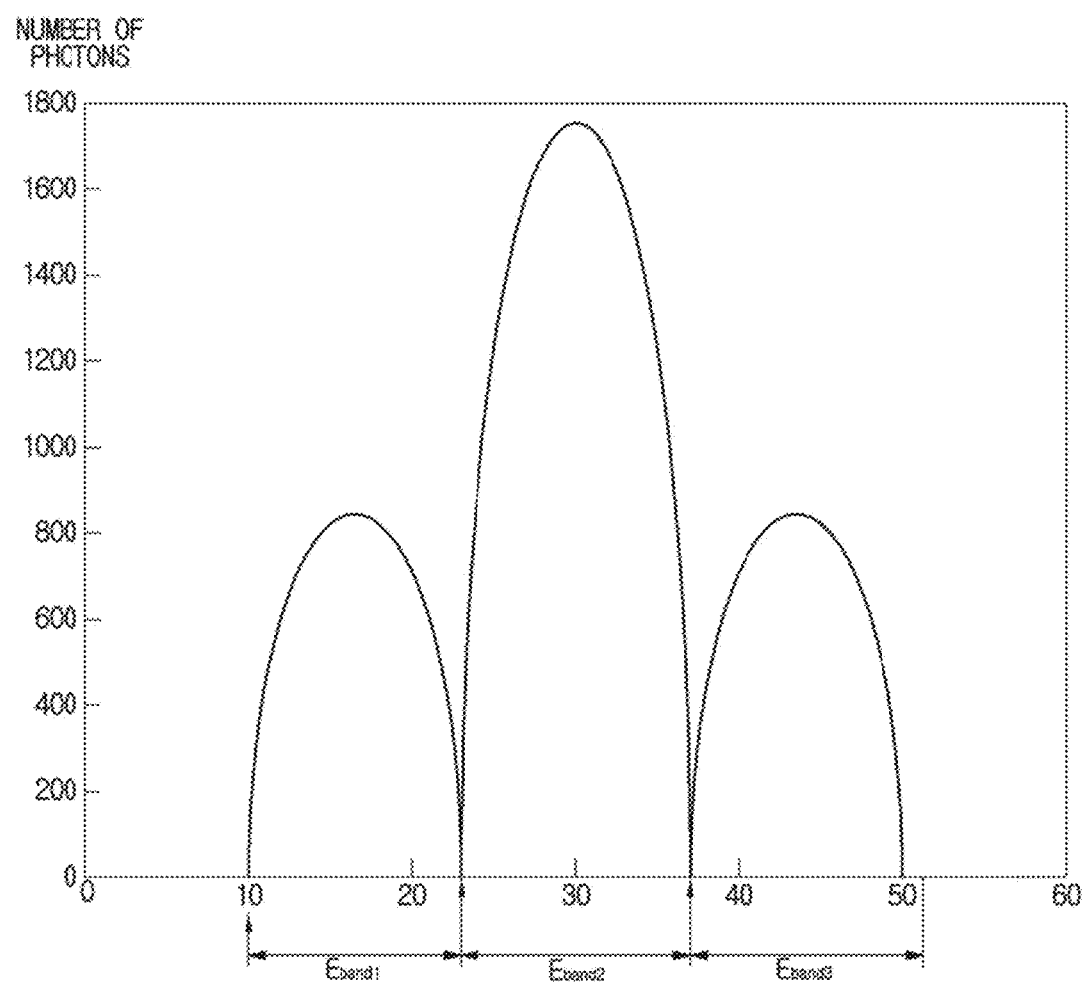
FIGS. 3A and 3B are graphs illustrating examples of an X-ray spectrum irradiated from an X-ray tube.
Figure 3B:
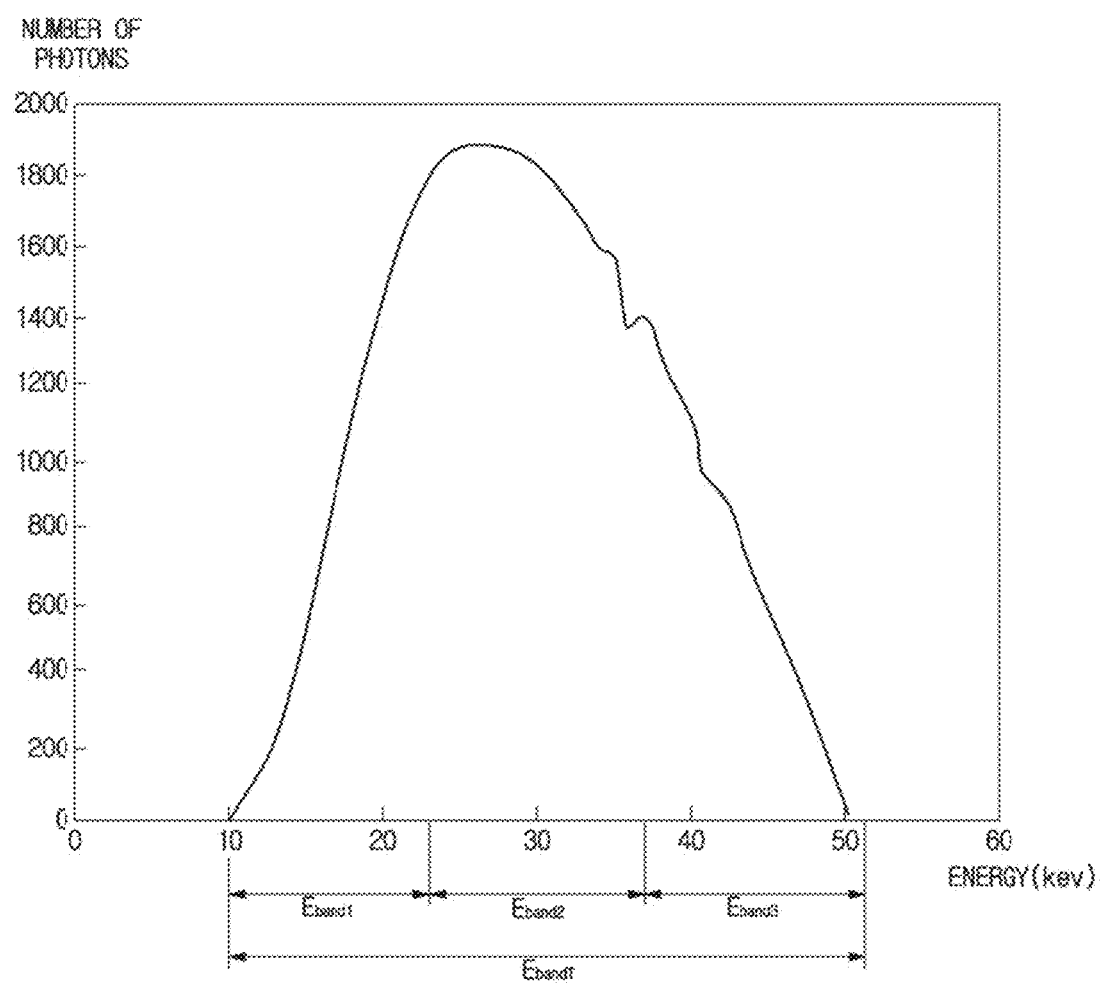

FIG. 2 is a diagram illustrating an internal structure of an X-ray tube, and FIGS. 3A and 3B are graphs illustrating examples of an X-ray spectrum irradiated from an X-ray tube.

An X-ray source 111 may include an X-ray tube 111a that generates X-rays. The X-ray tube 111a may be implemented as a bipolar vacuum tube including an anode 111c and a cathode 111e. The cathode 111e includes a filament 111h and a focusing electrode 111g to focus electrons, and the focusing electrode 111g may also be referred to as a focusing cup.

A vacuum tube 111k may be evacuated to a high vacuum state of about 10 mmHg and the filament 111h of the cathode 111e may be heated to a high temperature to generate thermoelectrons. The filament 111h may be, for example, a tungsten filament and may be heated by applying a current to an electrically conductive wire 111f connected to the filament 111h.

The anode 111c may include, for example, copper (Cu), and a target material 111d is coated or disposed on a surface of the anode 111c facing the cathode 111e. As the target material 111d, high-resistance materials such as chromium (Cr), iron (Fe), cobalt (Co), Nickel (Ni), tungsten (W), or molybdenum (Mo) may be used. The target material 111d is inclined at a certain angle, and the size of a focal point may be reduced along with an increase in the inclined angle. In addition, the size of the focal point may vary according to a tube voltage, a tube current, a size of the filament, a size of the focusing electrode, and a distance between the anode 111c and the cathode 111e.

When a high voltage is applied between the cathode 111e and the anode 111c, the thermoelectrons are accelerated and collide with the target material 111d of the anode 111c, thereby generating X-rays. The generated X-rays are radiated to the outside through a window 111i that may include a thin beryllium (Be) film. Although not shown, a filter may be located on a front or rear surface of the window 111i to filter X-rays having a certain energy band.

The target material 111d may be rotated by a rotor 111b. When the target material 111d is rotated, a heat accumulation rate per unit area may be increased by about ten times or more and the size of the focal point may be reduced, when compared to a case in which the target material 111d is fixed.

A voltage applied between the cathode 111e and the anode 111c of the X-ray tube 111a may be referred to as a tube voltage, and the magnitude of the tube voltage may be represented as peak kilovolts (kvp). When the tube voltage is increased, the speed of thermoelectrons is increased and thus the energy of X-rays (or the energy of photons) generated due to the collision of the thermoelectrons with the target material 111d is increased. A current flowing in the X-ray tube 111a is referred to as a tube current and may be represented as average current (mA). When the tube current is increased, the number of thermoelectrons radiated from the filament is increased and thus the dose of X-rays (or the number of X-ray photons) generated due to the collision of the thermoelectrons with the target material is increased. Accordingly, the energy of X-rays may be controlled by the tube voltage and the intensity or the dose of X-rays may be controlled by the product (mAs) of the tube current (mA) and an X-ray exposure time (s).

When irradiated X-rays have a predetermined energy band, the energy band may be defined by an upper limit and a lower limit. When at least one of the upper and lower limits of energy bands is different, the energy bands can be seen as mutually different energy bands. The upper limit of the energy band, i.e. the maximum energy of the irradiated X-rays may be adjusted by the magnitude of the tube voltage, and the lower limit of the energy band, i.e. the minimum energy of the irradiated X-rays may be adjusted by a filter. When the X-rays of the low energy band are filtered by using the filter, the average energy of the irradiated X-rays may be increased.

The X-ray source 111 may further include a filter that filters energy of a specific band as described above and a collimator that adjusts an FOV of X-rays, as well as the X-ray tube that generates X-rays to irradiate the generated X-rays.

As described above, to acquire the multi-energy X-ray image, the X-ray source 111 may irradiate X-rays of each energy band, and irradiate X-rays of the energy band including all of the individual energy bands.

For example, when acquiring X-ray images of a first energy band ($E_{band1}$)) a second energy band ($E_{band2}$), and a third energy band ($E_{band3}$), the X-ray source may respectively irradiate X-rays of the first energy band ($E_{band1}$), X-rays of the second energy band ($E_{band2}$), and X-rays of the third energy band ($E_{band3}$) as shown in FIG. 3A, and irradiate X-rays of an energy band ($E_{bandT}$) including all of the first energy band ($E_{band1}$), the second energy band ($E_{band2}$), and the third energy band ($E_{band3}$) as shown in FIG. 3B. Here, each energy band may be represented as average energy of the corresponding energy band, and hereinafter, in the exemplary embodiments which will be described below, the average energy of the first energy band ($E_{band1}$) is referred to as first energy, the average energy of the second energy band ($E_{band2}$) is referred to as second energy, and the average energy of the third energy band ($E_{band3}$) is referred to third energy.

In an example of FIG. 3A, the first energy band ($E_{band1}$), the second energy band ($E_{band2}$), and the third energy band ($E_{band3}$) are not overlapped with one another, however, these energy bands may be overlapped with one another. For example, the upper limit of the first energy band ($E_{band1}$) may be higher than the lower limit of the second energy band ($E_{band2}$), and the upper limit of the second energy band ($E_{band2}$) may be higher than the lower limit of the third energy band ($E_{band3}$).

The X-ray detector may adopt a charge integration mode that accumulates charges that are incident onto a single pixel for a predetermined time and then acquires electrical signals from the accumulated charges, or a photon counting mode in which a counting circuit is provided for each single pixel to count the number of photons having energy of a reference value or more. Hereinafter, the structure of the X-ray detector that adopts the photon counting mode will be described.

Figure 4:
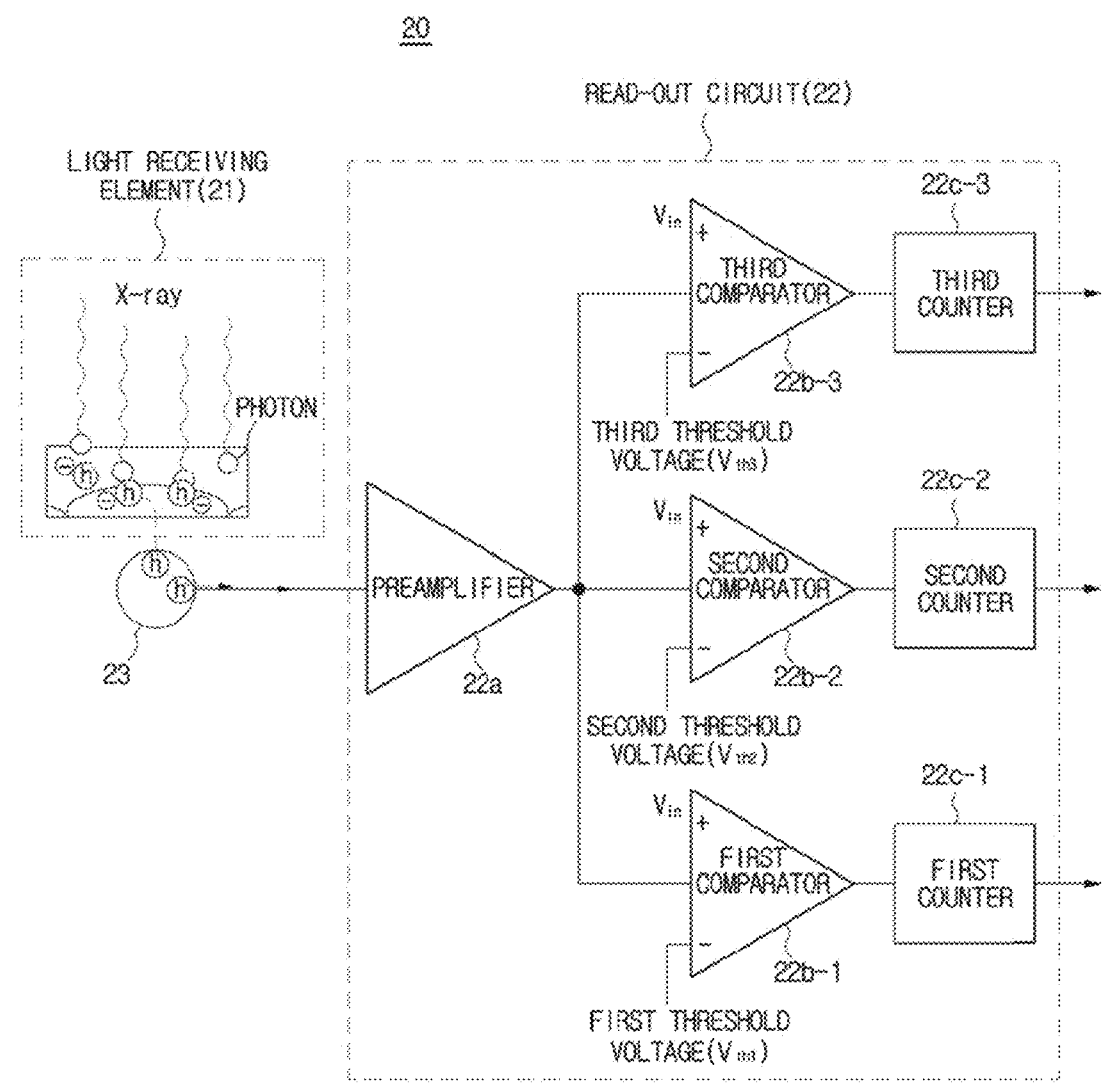
FIG. 4 is a schematic diagram illustrating a circuit configuration of a single pixel of an X-ray detector that separates detected X-rays for each energy band.

FIG. 4 is a diagram schematically illustrating a circuit configuration of a single pixel of an X-ray detector that separates detected X-rays for each energy band.

When the X-ray source 111 irradiates X-rays of the energy band ($E_{bandT}$) including all of the first energy band ($E_{band1}$), the second energy band ($E_{band2}$), and the third energy band ($E_{band3}$), the X-ray detector 112 may detect X-rays to separate the detected X-rays into X-rays of the first energy band ($E_{band1}$), X-rays of the second energy band ($E_{band2}$), and X-rays of the third energy band ($E_{band3}$), respectively.

To this end, as shown in FIG. 4, three comparison circuits are provided in a single pixel 20 constituting a second-dimensional array of the X-ray detector. Specifically, when electrons or holes generated from a light receiving element 21 by a single photon are output as voltage signals via a preamplifier 22a of a read-out circuit 22 connected to the light receiving element 21, the voltage signals ($V_{in}$) are input to first to third comparators 22b-1, 22b-2, and 22b-3.

Next, when first to third threshold voltages ($V_{th1}$), ($V_{th2}$) and ($V_{th3}$) are input to respective comparators 22b-1, 22b-2, and 22b-3, the first comparator (22b-1) compares the first threshold voltage ($V_{th1}$) and an input voltage ($V_{in}$), and a first counter 22c-1 counts the number of photons that cause the input voltage ($V_{in}$) to be larger than the threshold voltage ($V_{th1}$). In the same manner, a second counter 22c-2 counts the number of photons that cause the input voltage ($V_{in}$) to be larger than the second threshold voltage ($V_{th2}$), and a third counter 22c-3 counts the number of photons that cause the input voltage ($V_{in}$) to be larger than the third threshold voltage ($V_{th3}$).

Figure 5:
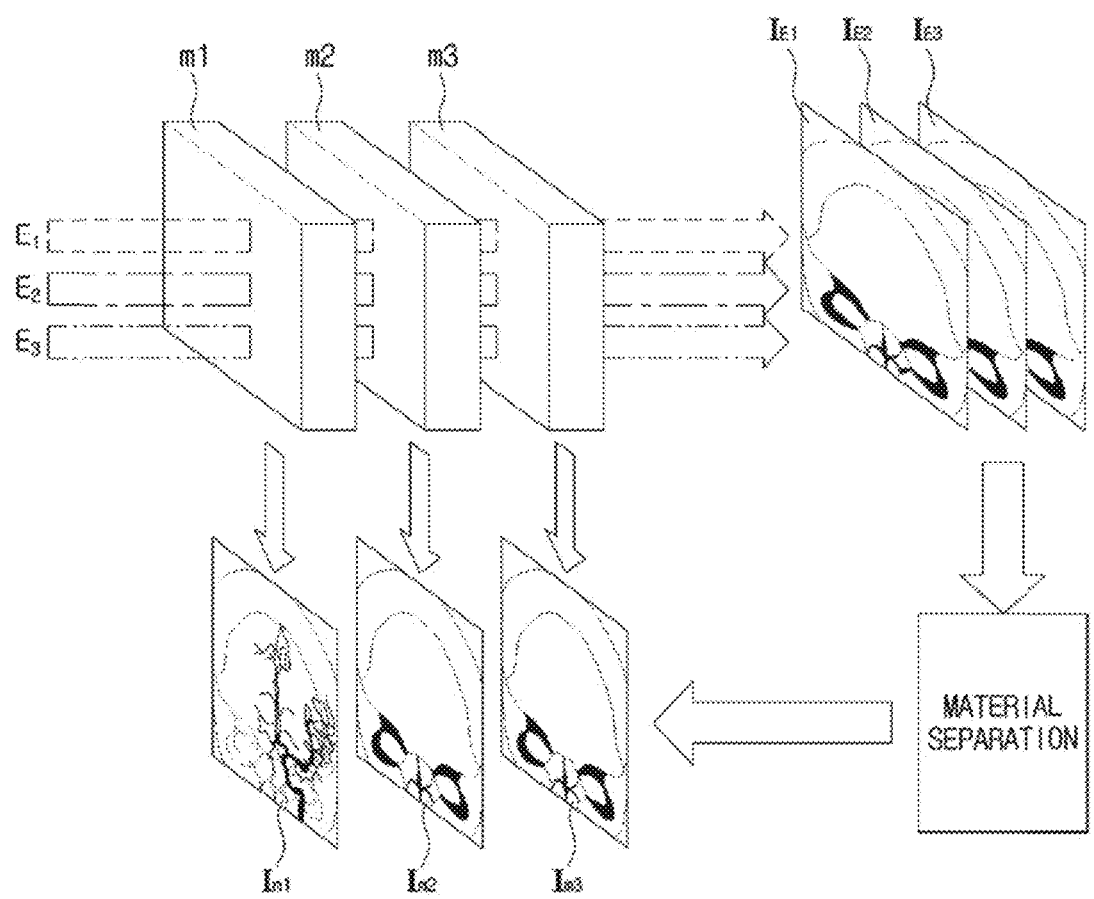
FIG. 5 is a schematic diagram illustrating material separation that is performed by an image processor according to an exemplary embodiment.

FIG. 5 is a schematic diagram illustrating material separation that is performed by an image processor according to an exemplary embodiment.

When the X-ray imaging apparatus 100 acquires a projection X-ray image, materials overlapped with one another in an X-ray irradiation direction among materials shown in the X-ray image may be difficult to be distinguished from each other in the projection X-ray image. In addition, materials having similar X-ray absorption characteristics may be difficult to be distinguished from each other in the X-ray image, regardless of the overlapping of the materials.

For example, when a first material $m_1$, a second material $m_2$, and a third material $m_3$ are overlapped with one another in the X-ray irradiation direction as shown in FIG. 5, the second material $m_2$ and the third material $m_3$ which are overlapped with each other behind the first material $m_1$ cannot be visually seen in the single energy X-ray image.

Thus, when the image acquirer 110 acquires a first energy X-ray image ($I_{E1}$), a second energy X-ray image ($I_{E2}$), and a third energy X-ray image ($I_{E3}$), the image processor 120 may separate the first material $m_1$, the second material $m_2$, and the third material $m_3$ by using the first energy X-ray image ($I_{E1}$), the second energy X-ray image ($I_{E2}$), and the third energy X-ray image ($I_{E3}$), and generate an image ($I_{m1}$) of the first material m1 in which the separated first material m1 is shown, an image ($I_{m2}$) of the second material m2 in which the separated second material m2 is shown, and an image ($I_{m3}$) of material in which the separated third material m3 is shown. Hereinafter, operations of the image processor 120 will be described in detail.

Figure 6:
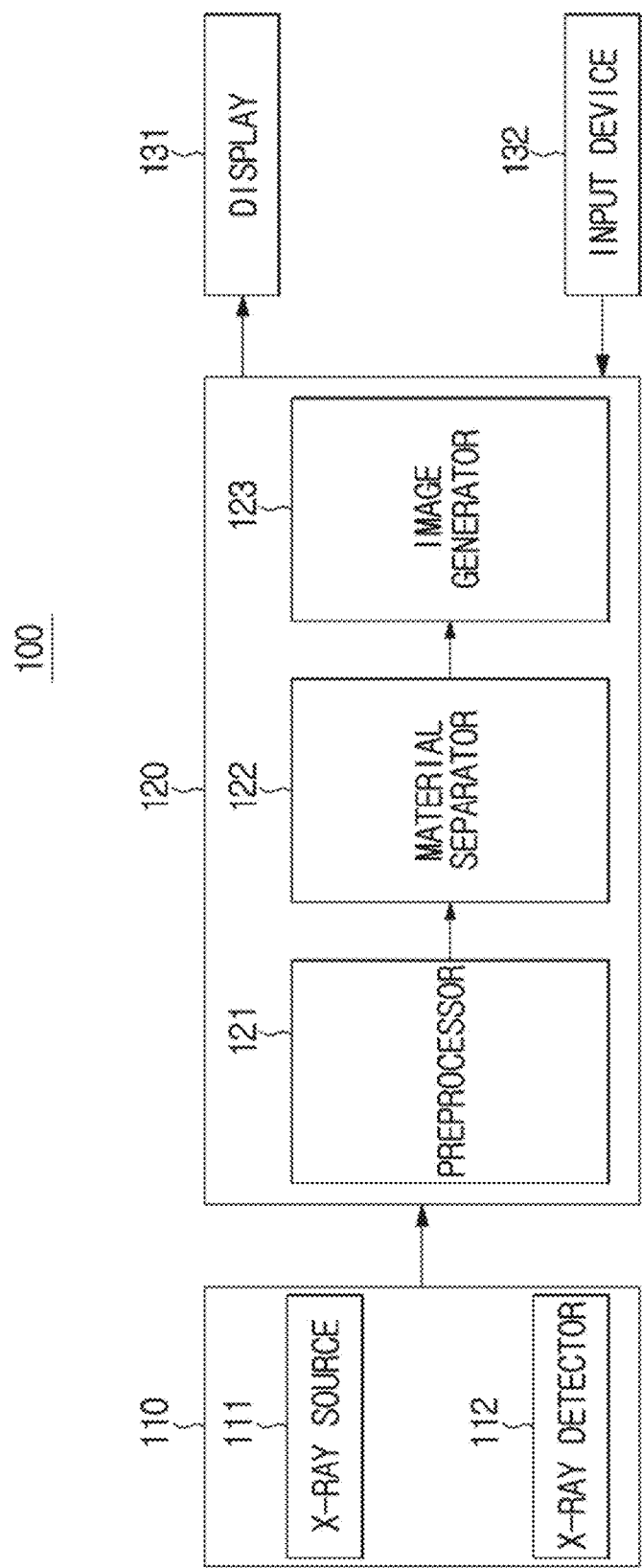
FIG. 6 is a control block diagram illustrating the structure of an image processor according to an exemplary embodiment.
Figure 7:
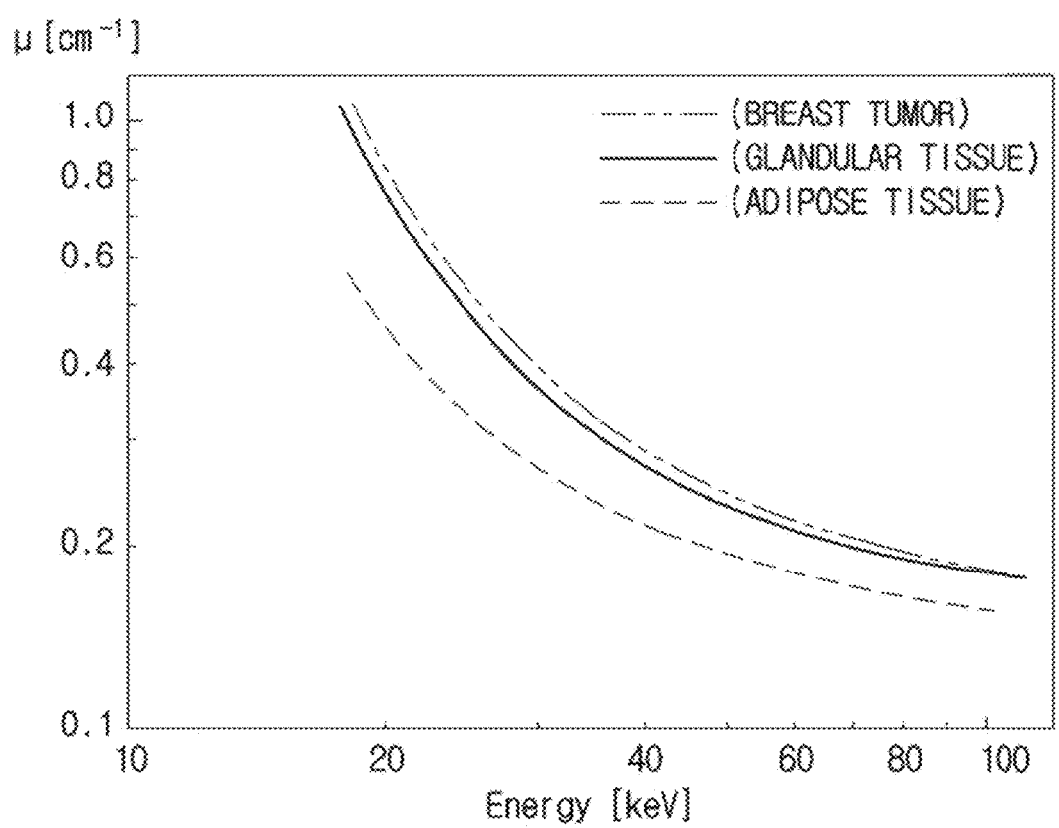
FIG. 7 is a diagram illustrating X-ray absorption characteristics of materials constituting the breast.

FIG. 6 is a control block diagram illustrating the structure of an image processor according to an exemplary embodiment, and FIG. 7 is a diagram illustrating X-ray absorption characteristics of materials constituting the breast.

Referring to FIG. 6, the image processor 120 may include a preprocessor 121 that performs preprocessing such as gain correction, offset correction, or the like with respect to a multi-energy X-ray image, a material separator 122 that acquires material information by performing material separation on the multi-energy X-ray image on which the preprocessing has been performed, and an image generator 123 that generates an image by using the acquired material information.

The X-ray image is generated by using X-ray absorption characteristics of the material, and X-ray attenuation is increased along with an increase in a thickness of the material. The X-ray absorption characteristics of the material may be represented as an attenuation coefficient (p), and the attenuation coefficient may be changed depending on the material. For example, soft tissues constituting a breast may include adipose tissues, glandular tissues, and a breast tumor, and the attenuation coefficients of these materials may have mutually different values as shown in FIG. 7.

Accordingly, the image processor 120 may model the X-ray image to an equation by using the thickness and attenuation coefficient of the material included in the FOV of the X-ray image, and acquire the thickness of the material by using the multi-energy X-ray image when information about the attenuation coefficient of the material is provided in advance. In other words, the material information acquired by performing material separation by the material separator 122 may be the thickness of the material.

Specifically, the following Equation 1 is an equation obtained by modeling the relationship between the intensity of X-rays incident to the X-ray detector and X-ray absorption characteristics of materials constituting an object.

$$I(E_i) = I_0(E_i)\exp\left[-\sum_{j=1}^{n} \mu_j(E_i)T_j\right] \quad \text{[Equation 1]}$$

Here, i denotes an index for the energy of X-rays, j denotes an index for the type of a material, and $\mu_j(E_i)$ denotes an attenuation coefficient of a material having the index j with respect to X-rays of the energy having the index i. $T_j$ denotes a thickness of the material having the index j, and n denotes a total number of materials desired to be separated. $I(E_i)$ denotes X-ray detection intensity of the energy having the index i, $I_0(E_i)$ denotes X-ray incident intensity (i.e., X-ray intensity before passing through the object) of the energy having the index i.

A pixel value $I_i$ of the multi-energy X-ray image may be defined by the following Equation 2, and the thickness of the material may be obtained by calculating a matrix operation of the following Equation 3.

$$I_i = \ln\frac{I_0(E_i)}{I(E_i)} \quad \text{[Equation 2]}$$

$$I = \mu \cdot T \quad \text{[Equation 3]}$$

For example, when X-ray images of three energy bands are obtained to separate three different types of materials, that is, when i={1, 2, 3} and j={1, 2, 3} are satisfied in Equation 1, thicknesses $T_1$, $T_2$, and $T_3$ of the materials may be obtained by performing an inverse matrix operation of the following Equation 4. Values of Equation 4 except T may be values which are all measured or provided in advance.

$$\begin{bmatrix} T_1 \\ T_2 \\ T_3 \end{bmatrix} = \begin{bmatrix} \mu_1(E_1) & \mu_2(E_1) & \mu_3(E_1) \\ \mu_1(E_2) & \mu_2(E_2) & \mu_3(E_2) \\ \mu_1(E_3) & \mu_2(E_3) & \mu_3(E_3) \end{bmatrix}^{-1} \begin{bmatrix} I_1 \\ I_2 \\ I_3 \end{bmatrix} \quad \text{[Equation 4]}$$

The multi-energy X-ray image provided to the material separator 122 may not be an image on which a logarithm operation has been performed. In other words, the pixel value of the multi-energy X-ray image may be defined as $I_0(E_i)/I(E_i)$. The material separator 122 may acquire required information from the multi-energy X-ray image, regardless of the type of the provided multi-energy X-ray image.

Referring again to FIG. 7, the adipose tissues, the glandular tissues, and the breast tumor constituting the soft tissues of the breast have different attenuation coefficients from one another, but do not have a substantial difference thereamong over the entire energy band. In particular, the attenuation coefficients of the glandular tissues and the breast tumor are substantially similar to each other. Thus, the glandular tissues and the breast tumor may not be easily distinguished from each other in a single energy X-ray image, but when performing material separation according to an exemplary embodiment, even materials having similar attenuation coefficients can be clearly distinguished from one another.

Figure 8:
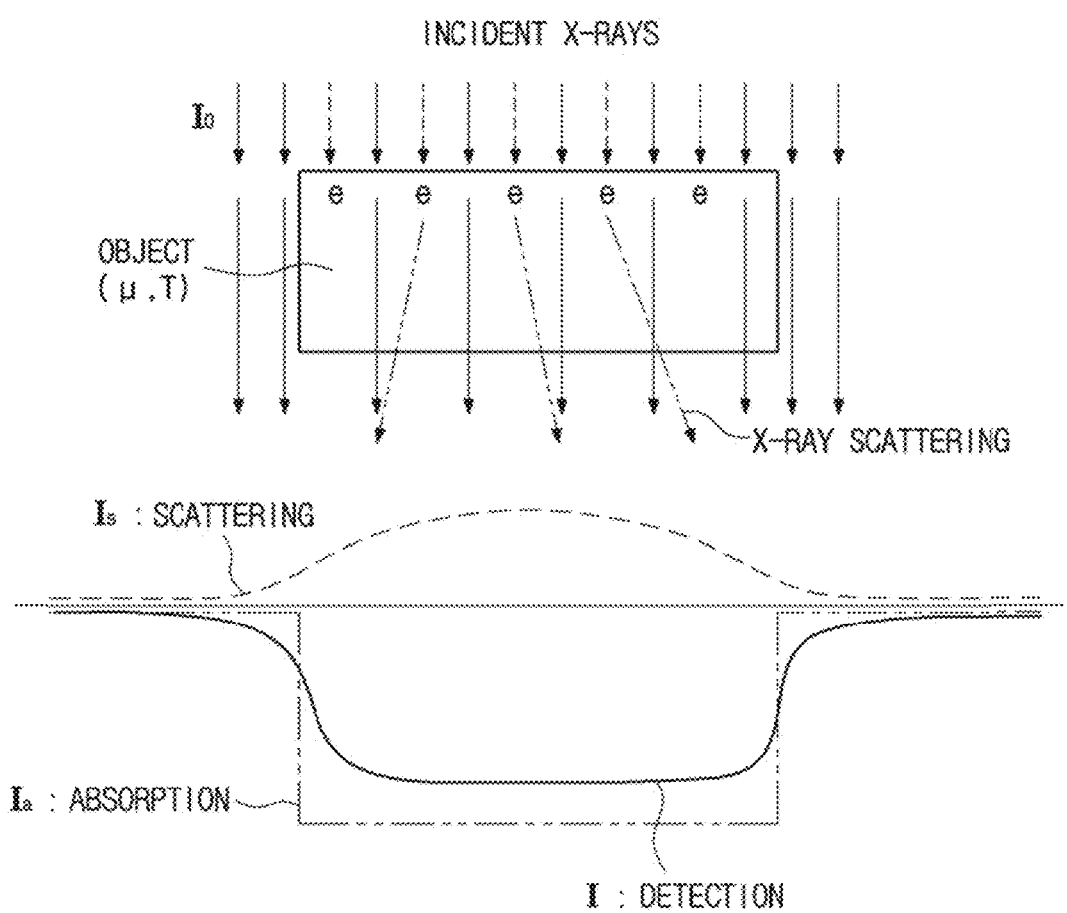
FIG. 8 is a schematic diagram illustrating X-ray scattering by materials constituting an object.
Figure 9:
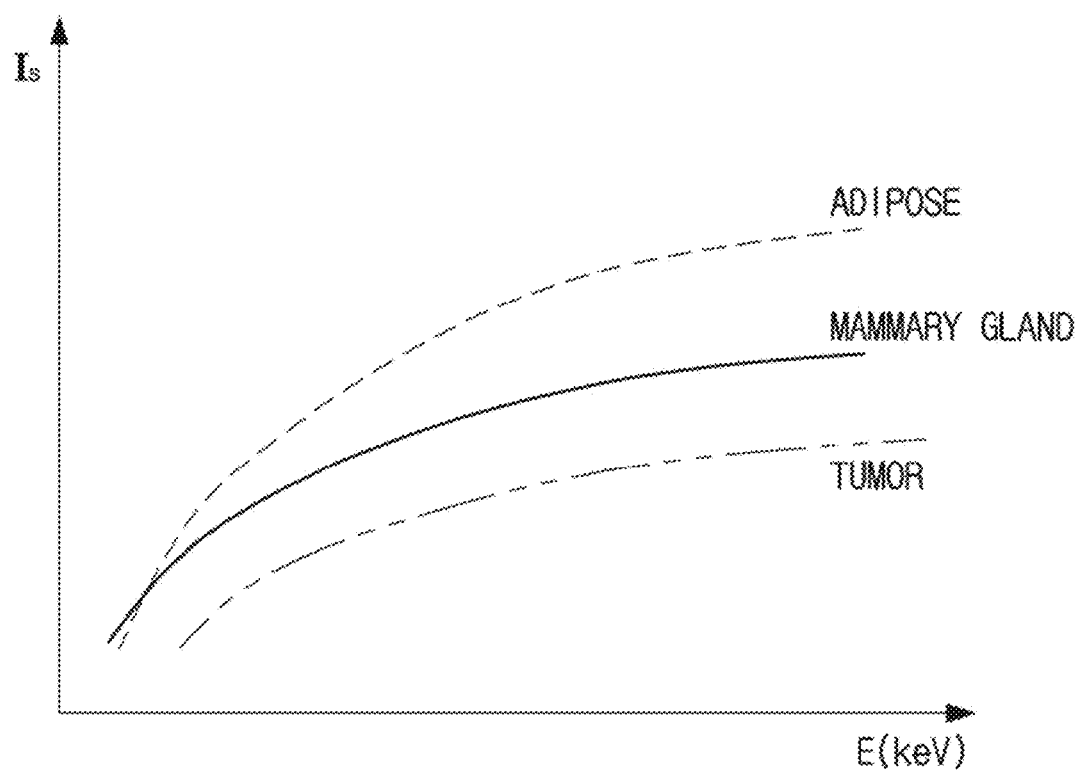
FIG. 9 is a diagram illustrating X-ray scattering characteristics for each material constituting the breast.

FIG. 8 is a schematic diagram illustrating X-ray scattering by materials constituting an object, and FIG. 9 is a diagram illustrating X-ray scattering characteristics for each material constituting the breast.

As shown in FIG. 8, a part of the X-rays irradiated from an X-ray source 111 may be scattered out of an intended path due to collisions with dust particles of the air, materials constituting an object, and the like before reaching an X-ray detector. Thus, in practice, instead of considering only X-ray absorption ($I_a$) of the materials in determining X-ray detection sensitivity (I), X-ray scattering ($I_s$) as well as the X-ray absorption may be also considered in determining the X-ray detection sensitivity (I). The relationship between the X-ray scattering and the X-ray detection sensitivity (I) may be represented by the following Equation 5.

$$I(E_i) = I_0(E_i)\exp\left[-\sum_{j=1}^{n}\mu_j(E_i)T_j\right] + I_s(E_i) \qquad \text{[Equation 5]}$$

Thus, the material separator 122 performs scattering correction together with material separation. By performing scattering correction together with material separation, it is possible to more accurately separate materials. Scattering correction may refer to removing (or substantially removing) X-ray scattering from the X-ray image, and to this end, $I_i$ used in Equation 4 is obtained by using the following Equation 6 rather than Equation 2.

$$I_i = \ln\frac{I_0(E_i) - I_s(E_i)}{I(E_i)} \qquad \text{[Equation 6]}$$

X-ray scattering ($I_s$) needs to be estimated to correct scattering, and the estimation of X-ray scattering ($I_s$) needs to be performed through simulation. X-ray scattering characteristics may vary for each material similarly to the case with the X-ray absorption characteristics. By way of example, X-ray scattering ($I_s$) is understood to have a different degree for each of adipose, a mammary gland, and a breast tumor which are materials constituting the breast, as shown in FIG. 9. There may be various types of factors used in simulation. For example, a thickness of a material, a scattering vector, a length of a scattering path, a location of the X-ray detector, response characteristics of the X-ray detector, and the like may be used as the factors in simulation.

When correcting X-ray scattering, accurate material separation is possible. However, as described above, scattering characteristics are different for each material constituting the object, and therefore accurate scattering estimation is difficult without accurate material separation. Thus, the material separator may perform material separation and scattering correction, which are interdependent, in a cyclic iterative manner, thereby improving the accuracy of material separation and scattering correction.

Figure 10:
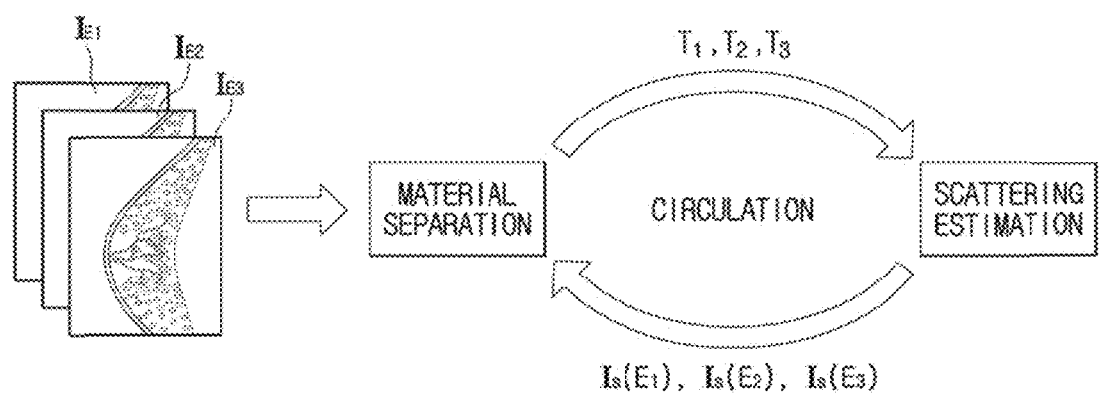
FIGS. 10 and 11 are diagrams schematically illustrating an operation in which a material separator performs material separation and scattering correction in a cyclic iterative manner according to exemplary embodiments.
Figure 11:
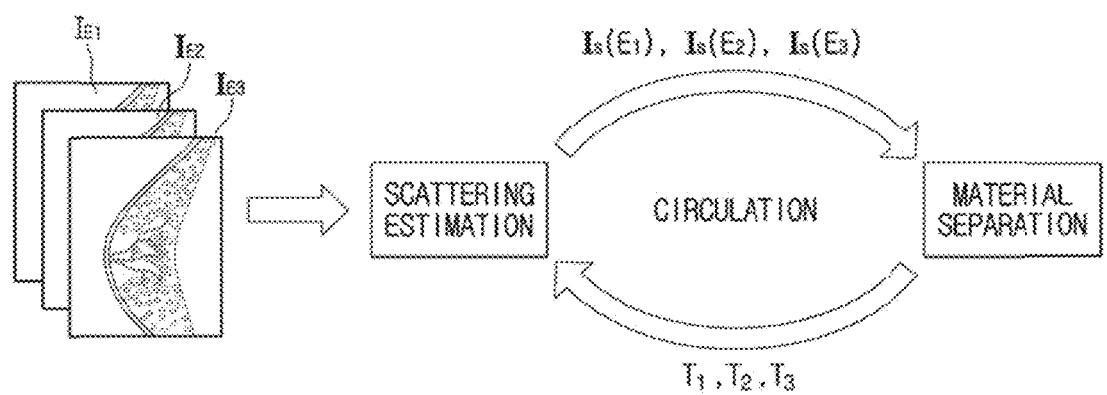

FIGS. 10 and 11 are diagrams graphically illustrating an operation in which a material separator performs material separation and scattering correction in a cyclic iterative manner according to exemplary embodiments. In examples of FIGS. 10 and 11, it is assumed that an object is the breast and materials to be separated include adipose, a mammary gland, and a breast tumor.

When a multi-energy X-ray image is transmitted to the material separator 122, the material separator 122 acquires thicknesses $T_1$, $T_2$, and $T_3$ of individual materials by performing material separation, and performs scattering correction by estimating X-ray scattering $I_s(E_1)$, $I_s(E_2)$, and $I_s(E_3)$ through simulation by using the thicknesses $T_1$ to $T_3$ of the materials, as shown in FIG. 10. Next, the material separator 122 performs material separation again on the multi-energy X-ray image on which scattering correction has been performed to obtain new thicknesses of the materials, and performs scattering estimation and scattering correction again by using new thicknesses of the materials acquired through material separation. This process may be performed in a cyclic iterative manner until the final results have a certain level of reliability.

As another example, as shown in FIG. 11, the material separator 122 may first estimate X-ray scattering $I_s(E_1)$, $I_s(E_2)$, and $I_s(E_3)$ to perform scattering correction, and then perform material separation to obtain thicknesses $T_1$, $T_2$, and $T_3$ of individual materials. The material separator 122 may perform scattering estimation and scattering correction again by using the thicknesses $T_1$, $T_2$, and $T_3$ of the materials acquired through material separation, and perform material separation again on the multi-energy X-ray image on which scattering correction is performed. Similarly to the case with the above-described example of FIG. 10, this process may be in a cyclic iterative manner until the final results have a certain level of reliability.

To summarize, the material separator 122 may first perform material separation, and then perform scattering correction as shown in the example of FIG. 10, or the material separator 122 may first perform scattering correction, and then perform material separation as shown in the example of see FIG. 11.

Referring again to Equation 5, values except for $T_j$ and $I_s(E_i)$ can be obtained through measurement, detection, or modeling. To separate a first material $m_1$, a second material $m_2$, and a third material $m_3$ which are three different types of materials, a case of using a first X-ray image $I_{E1}$, a second X-ray image $I_{E2}$, and a third energy X-ray image $I_{E3}$ which are acquired by the image acquirer 110 will be described.

When first performing material separation as shown in FIG. 10, the material separator 122 may first acquire the thicknesses $T_1$, $T_2$, and $T_3$ of the individual materials, without considering X-ray scattering by using Equation 6. Next, the material separator 122 estimates X-ray scattering $I_s(E_i)$ by performing simulation using the acquired thicknesses $T_1$, $T_2$, and $T_3$ of the individual materials. Next, the material separator 122 performs scattering correction by removing the estimated X-ray scattering $I_s(E_i)$ from the multi-energy X-ray image, and acquires the thicknesses $T_1$, $T_2$, and $T_3$ of the individual materials again. Next, the material separator 122 repeatedly performs scattering estimation and material separation until the reliability of the acquired thicknesses can be ensured to a certain extent.

Alternatively, when first performing scattering correction as shown in FIG. 11, the material separator 122 first performs scattering estimation. Since there is no calculated thickness information, initial scattering estimation may be performed by using boundary detection and standard tissue composition that is given in advance. The material separator 122 performs scattering correction by removing the estimated X-ray scattering from the multi-energy X-ray image, and calculates the thicknesses $T_1$, $T_2$, and $T_3$ of the individual materials by using the multi-energy X-ray image on which scattering correction has been performed. Next, the material separator 122 estimates X-ray scattering by using the acquired thicknesses for simulation, and calculates the thicknesses of the individual materials again by using the multi-energy X-ray image on which the estimated X-ray scattering has been performed. Similarly, the material separator 122 repeatedly performs scattering correction and material separation until the reliability of the calculated thicknesses of the materials can be ensured to a certain extent.

The material separator 122 may set in advance verification conditions for determining whether the reliability can be ensured to a certain extent, and determine whether to continue to perform scattering correction and material separation according to whether the verification conditions are satisfied.

For example, whether a difference between calculated data and measured data is within a predetermined error range may be set as the verification condition. Specifically, when a difference between X-ray intensity calculated by applying the acquired thickness $T_i$ for each material and actually detected X-ray intensity is within a predetermined error range, the material separator 122 may stop the performing of scattering correction and material separation, and otherwise, continue to perform scattering correction and material separation.

As another example, whether a cost function is defined and the defined cost function is minimized may be set as the verification condition. The cost function may be defined by using the intensity of detected X-rays, a calculated thickness for each material, an effective absorption coefficient based on polychromatic X-rays, or the like. In this instance, the effective absorption coefficient may be obtained by considering a difference between an absorption coefficient for each material in an actual polychromatic X-ray environment and a theoretical absorption coefficient in a monochromatic X-ray environment, and measured through an appropriately designed phantom experiment.

The above-described verification conditions are merely examples which may be applied to the X-ray imaging apparatus 100 according to the exemplary embodiments, and other conditions such as whether material separation has been performed a prescribed number of times, and the like may be applied.

When material separation by the material separator 122 is completed, the image generator 123 may generate an image for providing a material separation result to a user. For example, the image generator may generate a material separation image to which a final thickness of each material acquired by the material separator 122 is applied and perform post-processing for improving image quality such as image enhancement, noise reduction, and the like, or the image generator 123 may generate a highlighted material image by applying weighted subtraction to the multi-energy X-ray image, and combine final thickness information of each material and the highlighted material image.

For example, when an object is the breast, the material separator 122 may perform the above-described scattering correction and material separation on the first energy X-ray image, the second energy X-ray image, and the third energy X-ray image in the cyclic iterative manner, thereby acquiring the thickness of each of adipose, a mammary gland, and a breast tumor of the breast. The image generator 123 may generate at least one of an adipose separation image, a mammary gland separation image, and a tumor separation image by using the thickness of each material, and display the generated image through the display 131.

Alternatively, the image generator 123 may generate at least one highlighted material image of an adipose emphasized image, a mammary gland emphasized image, and a tumor emphasized image by applying weighted subtraction to the first energy X-ray image, the second energy X-ray image, and the third energy X-ray image, and combine the thickness of each material and the generated highlighted material image. Here, weighted subtraction is a scheme which can acquire an image in which a desired image is emphasized by adding an appropriate weighted value to each of X-ray images acquired from mutually different energy bands and then subtracting the added weighted value, based on the fact that a difference in X-ray attenuation characteristics among materials varies for each energy band. For example, when a lesion emphasized image is generated by applying weighted subtraction, it is possible to more clearly display boundaries between the corresponding lesion and the other regions from the lesion emphasized image by using thickness information of the corresponding lesion acquired through material separation, or adjusting brightness of the lesion emphasized image by considering the thickness information of the corresponding lesion.

The image processor 120 may include a memory that temporarily stores programs and data and a microprocessor that processes data according to the program stored in the memory. A separate memory and a microprocessor may be provided for each of the preprocessor 121, the material separator 122, and the image generator 123, or all or some of the components may share the memory and the microprocessor.

The operation of the image processor 120 may be controlled according to a user's command input through the input device 132. The user may select one of the material separation image and the highlighted material image, or select whether information about the separated material and the highlighted material image are to be combined.

Alternatively, the operation of the image processor 120 may be automatically controlled by the X-ray imaging apparatus 100. To this end, the X-ray imaging apparatus 100 may further include a controller that controls the image processor 120, and this will be described with reference to FIG. 12.

Figure 12:
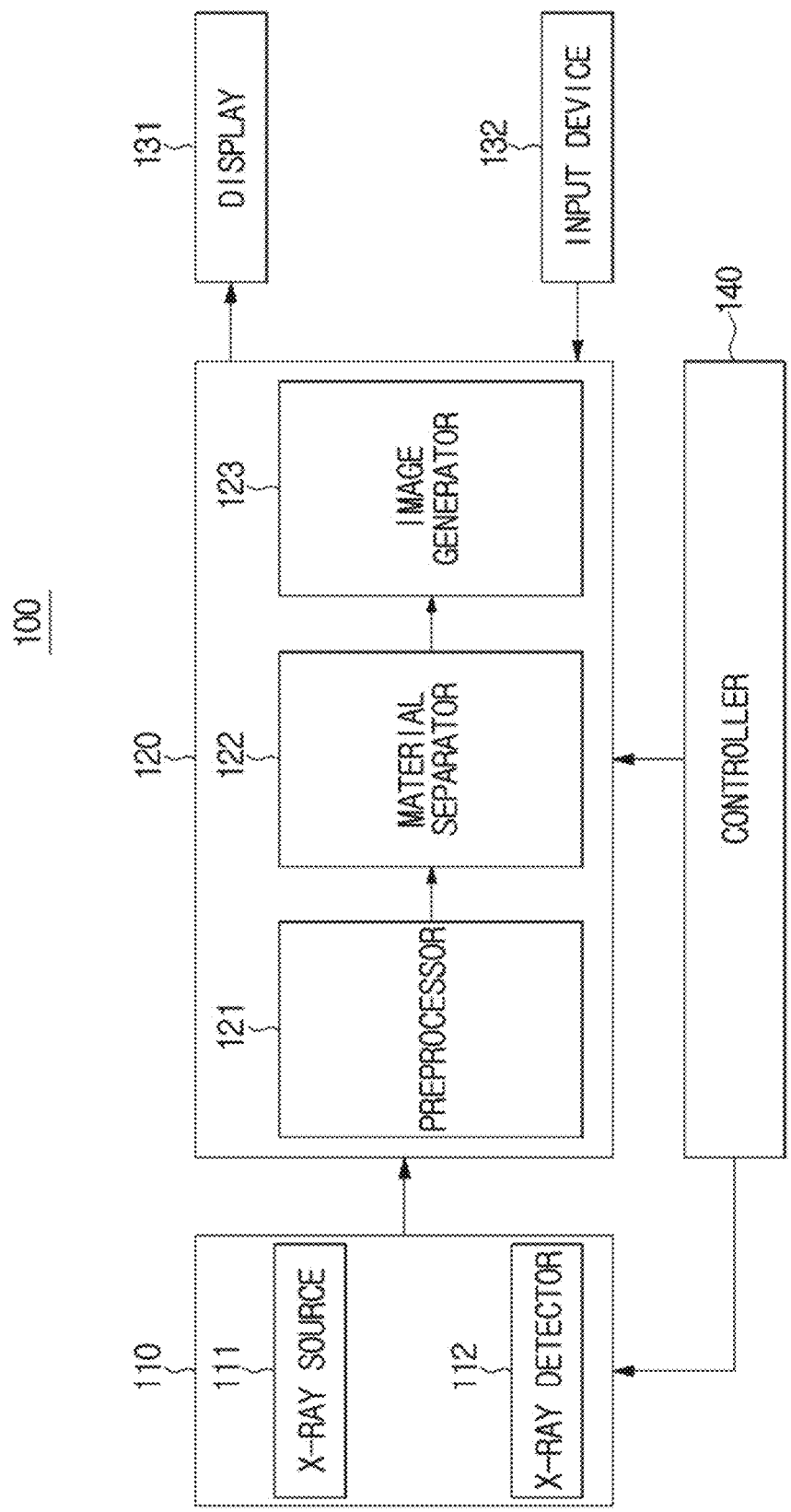
FIG. 12 is a control block diagram illustrating an X-ray imaging apparatus that further includes a controller according to an exemplary embodiment.
Figure 14:
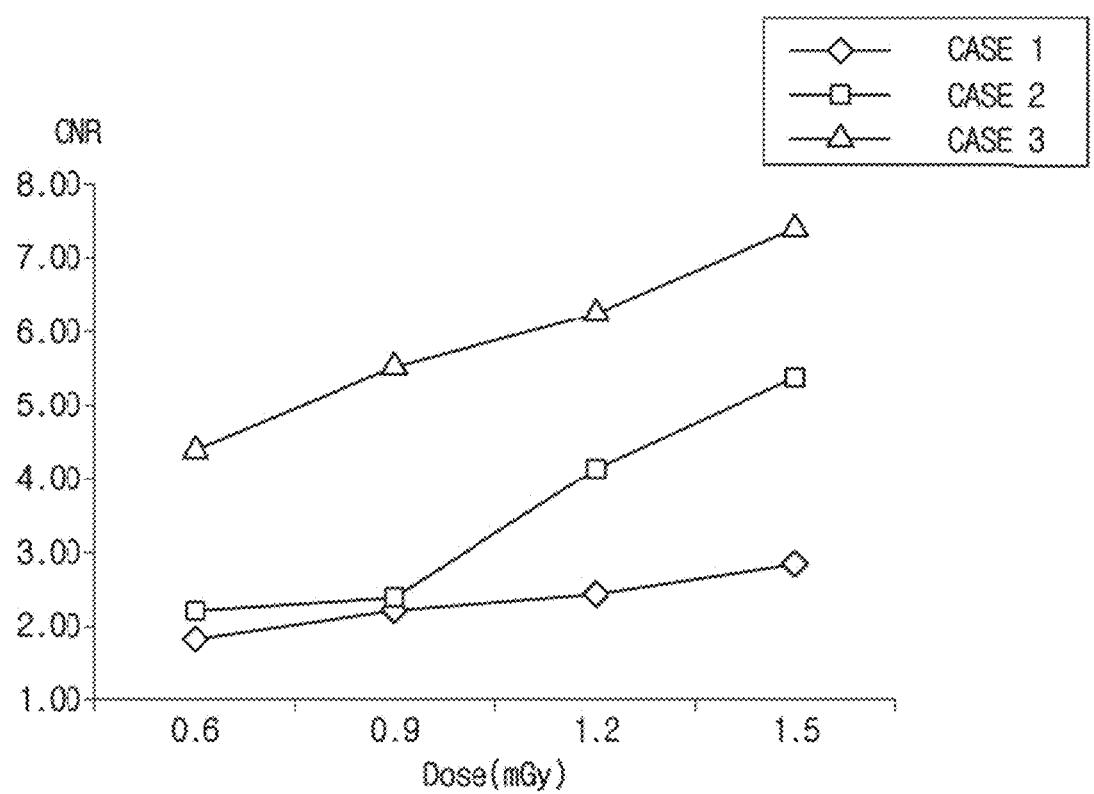

FIG. 12 is a control block diagram illustrating an X-ray imaging apparatus that further includes a controller according to an exemplary embodiment.

Referring to FIG. 12, the X-ray imaging apparatus 100 may further include a controller 140 that controls the operation of the image processor 120.

The controller 140 may select at least one of the material separation image and the highlighted material image based on at least one of the imaging parameters of the X-ray image to be displayed on the display 131, or select whether the information about the separated material and the highlighted material image are to be combined to be displayed on the display 131. Here, the imaging parameter may include the dose of X-rays. An X-ray image acquired in a lower dose environment has a lower signal-to-noise ratio (SNR), and therefore it is difficult to distinguish materials from one another. Thus, the controller 140 may select the material separation image when a dose applied to the imaging of the X-ray image is less than a predetermined reference dose, and select the highlighted material image when the dose is the reference dose or more. When the material separation image is selected by the controller 140, the image processor 120 may acquire material information by performing the above-described scattering correction and material separation in the cyclic iterative manner. Next, the image processor 120 may generate the material separation image by using the acquired material information, or combine the acquired material information and the highlighted material image.

In addition, the controller 140 may control the operation of the image acquirer 110. For example, the controller 140 may perform auto exposure control (AEC) for automatically controlling the imaging parameters such as a tube voltage, a tube current, a type of a target material of an anode, a type of a filter, an FOV, an exposure time, and the like, and to this end, the controller 140 may first perform pre-imaging (preshot) of the object. For example the controller 140 may be implemented as a processor such as a central processor unit (CPU), a micro controller unit (MCU), or a micro processor unit (MPU).

FIGS. 13 to 17 are diagrams illustrating simulation results of an X-ray imaging apparatus according to an exemplary embodiment.

FIG. 13 illustrates simulation results of case 1, which is a case of acquiring a single energy X-ray image of the breast, case 2, which is a case of performing material separation once by using a multi-energy X-ray image of the breast, and case 3, which is a case of acquiring the multi-energy X-ray image of the breast by using the X-ray imaging apparatus 100 and performing material separation and scattering correction in the cyclic iterative manner.

X-ray images were captured with respect to case 1, case 2, and case 3 based on the dose of X-rays, which was respectively 0.6 mGy, 0.9 mGy, 1.2 mGy, and 1.5 mGy, and a contrast to noise ratio (CNR) of tumor tissue to glandular tissue was measured. Then, the simulation results are quantitatively shown in the table of FIG. 13 and the graph of FIG. 14.

Referring to the table of FIG. 13, from the dose of 1.2 mGy which is generally used, CNRs of case 1, case 2, and case 3 were measured as 2.46, 4.16, and 6.30, respectively. Thus, it can be seen that, compared to a case (case 2) in which material separation has been performed by acquiring the multi-energy X-ray image from the same dose, a case (case 3) in which material separation and scattering correction have been performed in the cyclic iterative manner has a CNR that is increased by about 50%.

In addition, the CNR of case 2 was measured as 4.16 when the dose was 1.2 mGy, and the CNR of case 3 was measured as 4.45 when the dose was 0.6 mGy. Thus, it can be confirmed that, when performing material separation and scattering correction in the cyclic iterative manner, the dose can be reduced by half while maintaining approximately the same image quality as compared to when performing simple material separation.

In other words, in a case in which material separation is performed according to the above-described exemplary embodiment, it is possible to improve the accuracy of material separation even when performing imaging with low dose X-rays. Thus, the X-ray imaging apparatus can capture moving images that require continuous X-ray exposure of an object, as well as still images.

Figure 15:
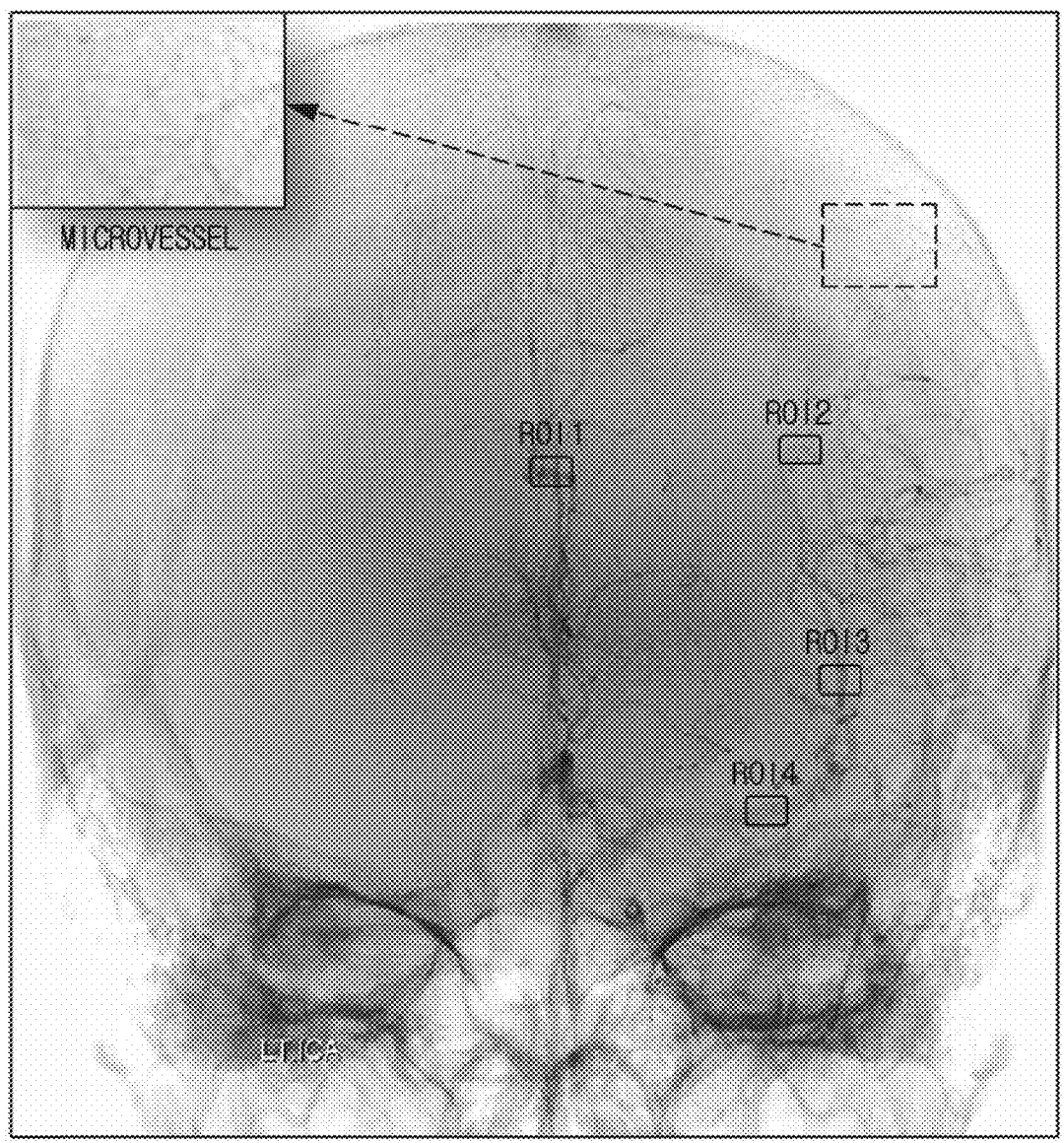
Figure 16:
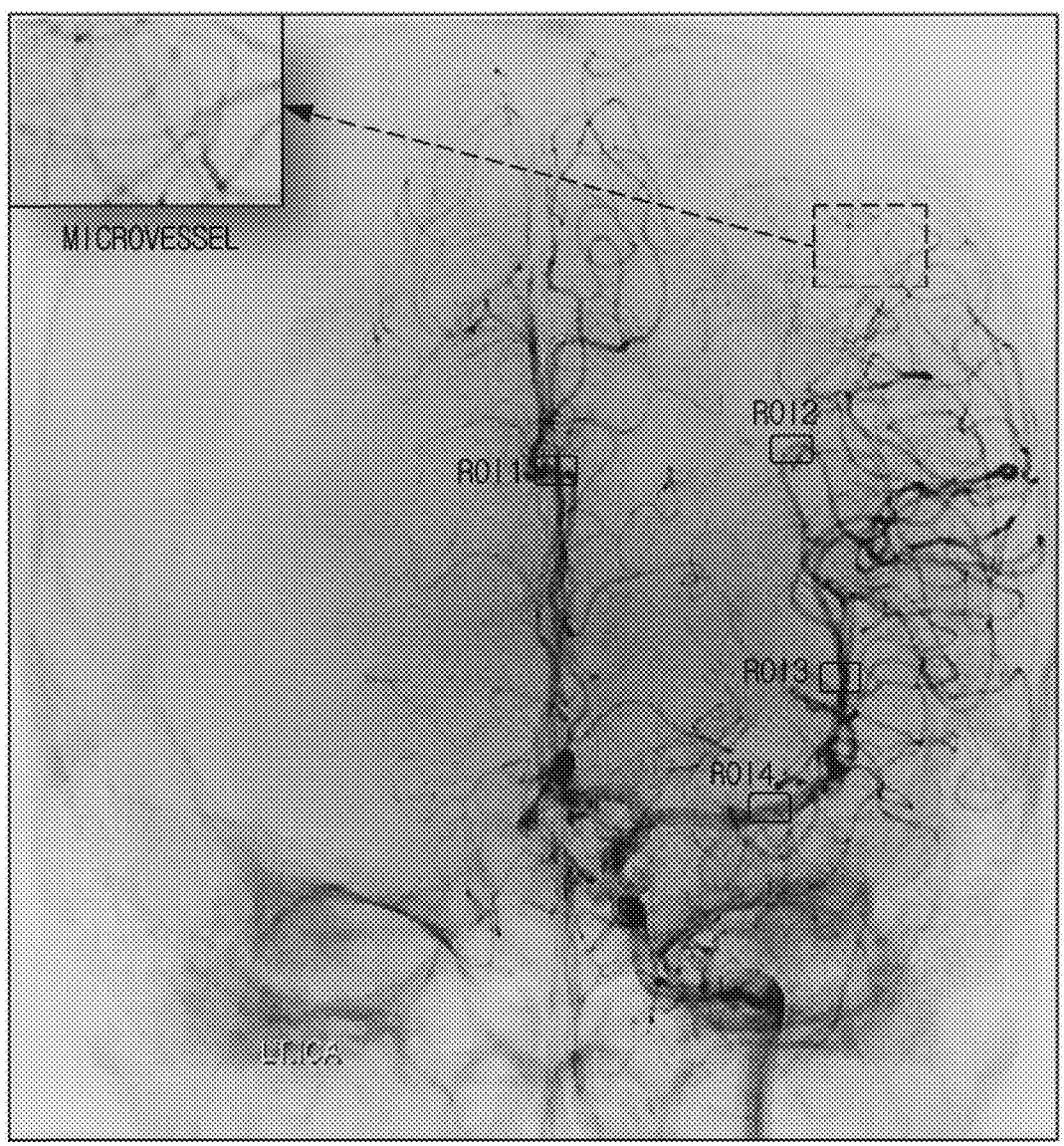
Figure 17:
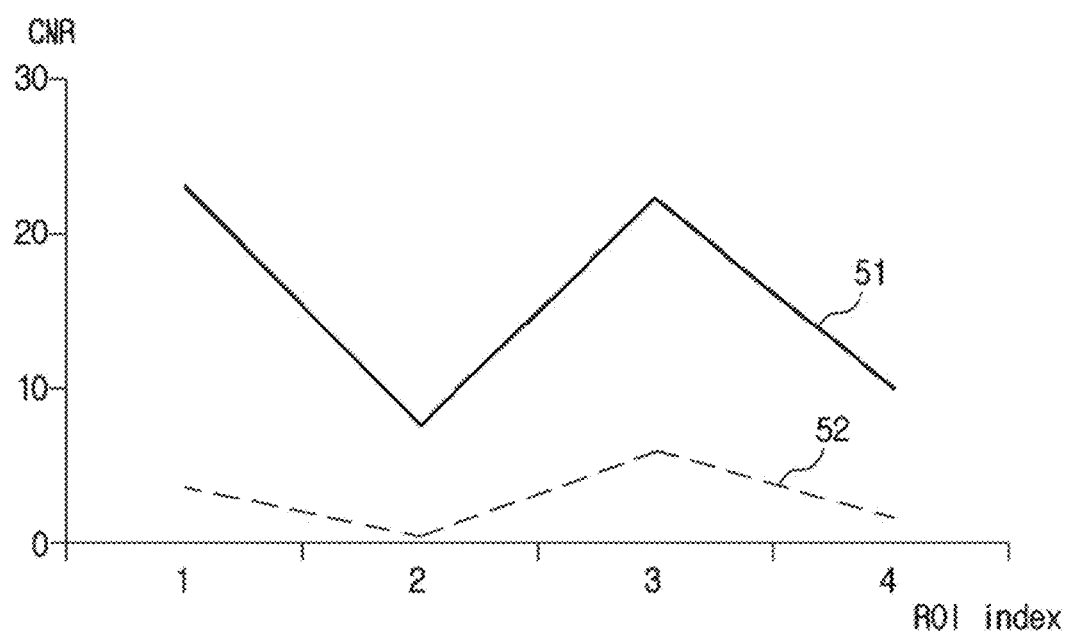

FIG. 15 is a single frame image of X-ray moving images of a brain that was captured with single energy X-rays, and FIG. 16 is an image in which blood vessels are separated by capturing X-ray moving images by the X-ray imaging apparatus 100 and performing material separation and scattering correction in the cyclic iterative manner. FIG. 17 is a graph showing a result obtained by measuring a CNR of a region of interest (ROI) to a background region from the image of FIG. 16. Here, the region of interest corresponds to a blood vessel region.

First, when comparing frame images of FIGS. 15 and 16, it can be confirmed that the blood vessel is more clearly visible in the image of FIG. 16 that is obtained by performing material separation and scattering correction in the cyclic iterative manner according to an exemplary embodiment. In addition, it can be confirmed with the naked eye that micro-vessels which are enlarged and displayed in each image are also more clearly distinguished in the image of FIG. 16.

When material distinction between two materials is defined as a quantitative value, it can be seen that a CNR 51 of the region of interest that was measured in the image of FIG. 16 obtained by performing material separation and scattering correction in the cyclic iterative manner was excellent, as shown in FIG. 17. In particular, in the case of region of interest 1, a CNR that is approximately seven times higher than a CNR 52 of a single energy X-ray image was measured.

Hereinafter, various types of the X-ray imaging apparatus 100 will be described.

The structure or imaging method of the X-ray imaging apparatus 100 may vary depending on an imaged region, a type of an X-ray image, an imaging purpose, or the like. Specifically, as examples of the X-ray imaging apparatus 100, a general radiography device that images a chest, arms, legs, etc., a mammography device that images breasts, a fluoroscopy device that images X-ray moving images, a C-arm device that performs angiography, and the like may be given. The X-ray imaging apparatus according to an exemplary embodiment may be any one of the above-described X-ray imaging apparatuses, but is not limited thereto. Other than the above-described X-ray imaging apparatus, the X-ray imaging apparatus 100 may include any device as long as the device can image the inside of an object by using X-rays.

Figure 18A:
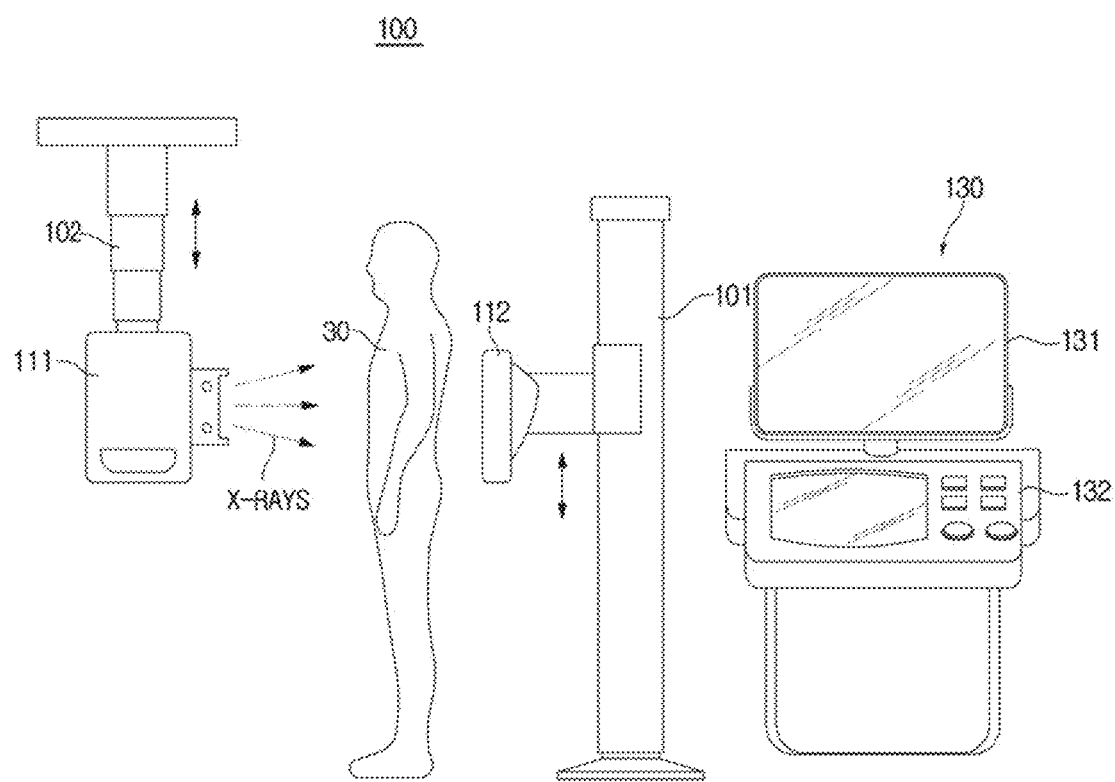
FIG. 18A is an appearance diagram illustrating a case in which an X-ray imaging apparatus according to an exemplary embodiment performs general radiography.
Figure 18B:
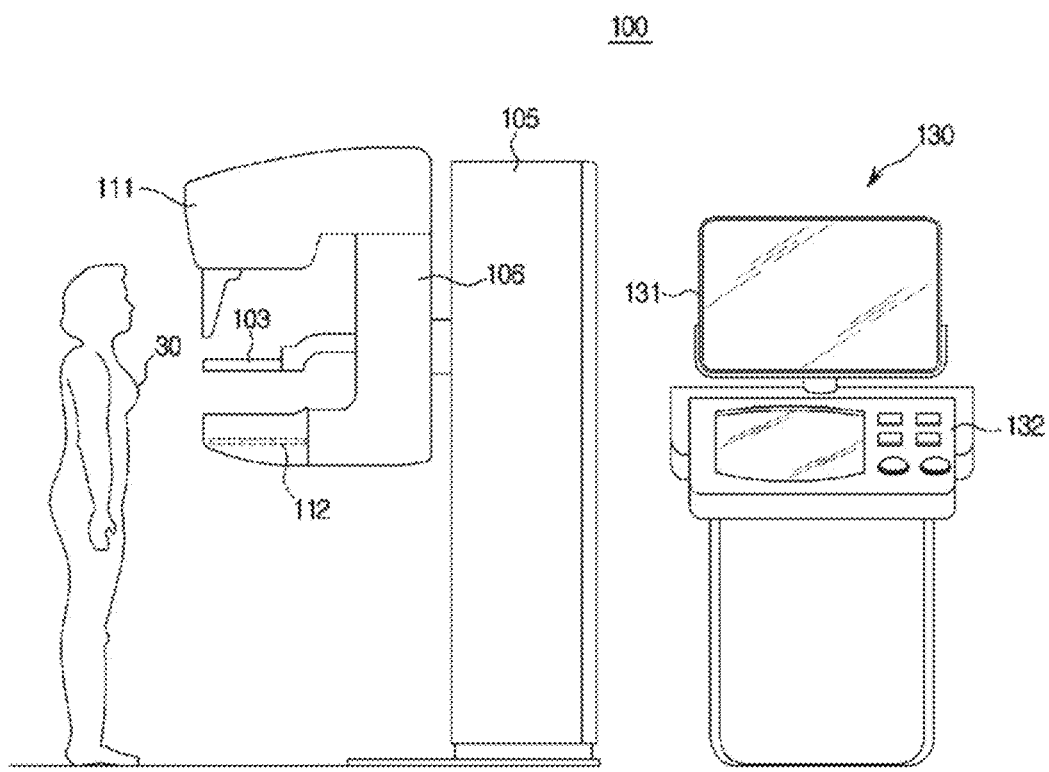
FIG. 18B is an appearance diagram illustrating a case in which an X-ray imaging apparatus according to an exemplary embodiment performs mammography.
Figure 18C:
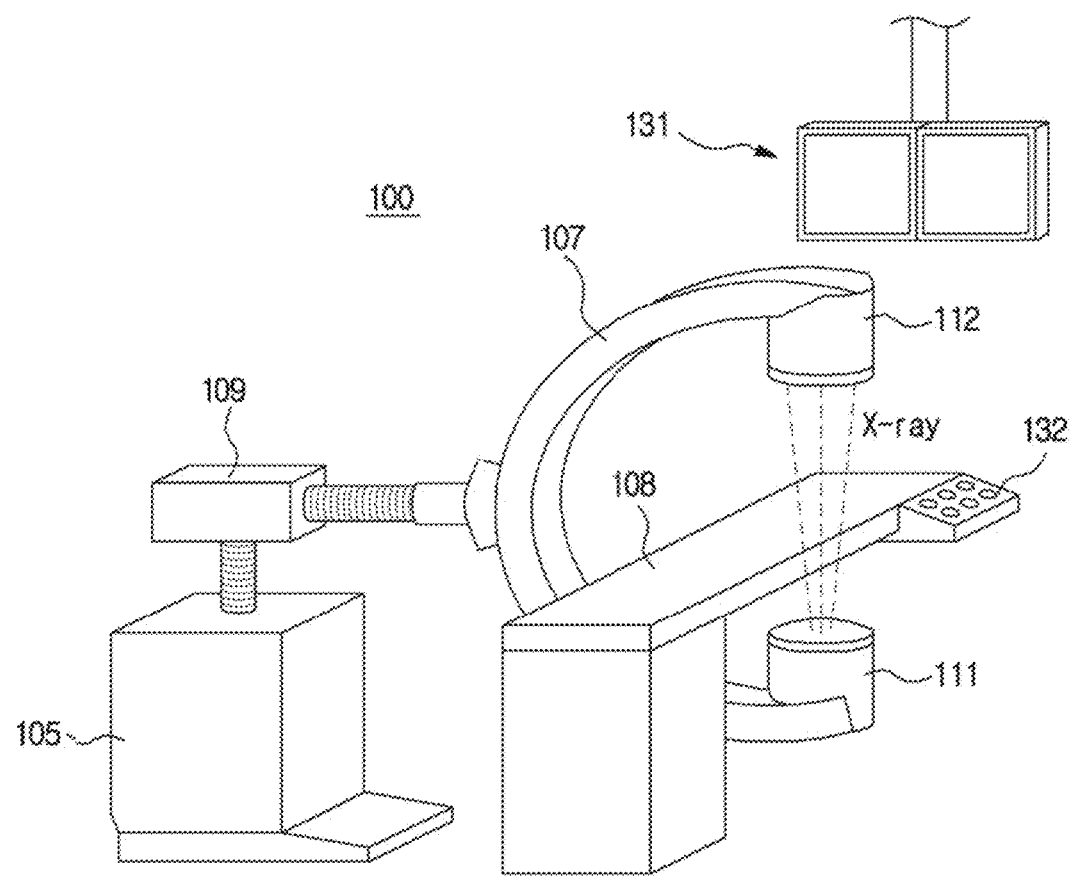
FIG. 18C is an appearance diagram illustrating a case in which an X-ray imaging apparatus according to an exemplary embodiment is a C-arm device.

FIG. 18A is a diagram illustrating a case in which an X-ray imaging apparatus according to an exemplary embodiment performs general radiography, FIG. 18B is a diagram illustrating a case in which an X-ray imaging apparatus according to an exemplary embodiment performs mammography, and FIG. 18C is a diagram illustrating a case in which an X-ray imaging apparatus according to an exemplary embodiment is a C-arm device.

When the X-ray imaging apparatus 100 performs general radiography, a region 30 to be imaged of a patient is located between an X-ray source 111 and an X-ray detector 112 as shown in FIG. 18A, and when the X-ray source 111 irradiates the region to be imaged with X-rays, the X-ray detector 112 detects X-rays transmitted through the region 30 to be imaged to generate an X-ray image. The region 30 to be imaged may be a region such as patient's chest, arms, legs, waist, or pelvis, and in the exemplary embodiment which will be herein described, the region 30 to be imaged is referred to as an object.

The X-ray source 111 may be mounted on a holder 102, and the holder 102 may be connected to the ceiling so that a length of the holder 102 can be adjusted. Thus, the X-ray source 111 mounted on the holder 102 may be moved up and down according to the object, and when the holder 102 is moved along guide rails mounted on the ceiling, the X-ray source 111 may be moved in a movement direction of the holder 102.

In an example of FIG. 18A, a stand type X-ray imaging apparatus 100 in which the X-ray detector 112 is mounted on a stand 101 and X-ray imaging is performed in a state in which the patient stands up is shown, but the X-ray imaging apparatus 100 in which the X-ray detector 112 is mounted on a table on which the patient can lie down and X-ray photography is performed in a state in which the patient lies down on the table may be used.

The display 131 and the input device 132 may be provided on a workstation 130. The workstation 130 is a device that controls overall operations of the X-ray imaging apparatus 100 and provides a user interface, and may be referred to as a host device. The display 131 may be implemented as a display device such as a light emission diode (LED) display, a liquid crystal display (LCD), a plasma display panel (PDP), an organic light emission diode (OLED) display, or the like, and the input device 132 may be implemented as buttons, keys, jog shuttle, trackball, mouse, or the like, or a touch panel.

The user may control exposure parameters such as a tube voltage, a tube current, a target material, a filter, a collimator, and the like by manipulating the input device 132, or execute auto exposure control (AEC) for automatically controlling imaging parameters by performing pre-imaging. In addition, the user may input a selection concerning whether to acquire a multi-energy X-ray image or a single energy X-ray image, or input a command for controlling the operation of the image processor 120 as described above.

The display 131 may display a guidance screen for guiding a user's input, or display the multi-energy X-ray image or the single energy X-ray image. After the image processor 120 performs material separation and scattering correction in the cyclic iterative manner by using the multi-energy X-ray image, the display 131 may display a material separation image, or display a combination of a highlighted material image generated through weighted subtraction and material information acquired through material separation.

When the X-ray imaging apparatus performs mammography, the breast 30 that is an object is located in an upper portion of the X-ray detector 112 as shown in FIG. 18B, and the X-ray source 111 irradiates an upper portion of the object with X-rays.

In this instance, to spread materials overlapped with one another in an X-ray irradiation direction as much as possible, it is possible to press the breast 30 by using a pressure paddle 103. The pressure paddle 103 may be mounted on a frame 106 to be moved vertically. The pressure paddle 103 may be moved manually by a user or automatically.

The X-ray source 111 and the X-ray detector 112 are connected to the frame 106, and the frame 106 is connected to a gantry 105, and in this instance, the frame 106 may be moved in a longitudinal direction of the gantry 105, so that the frame 106 may be aligned with the position of the object.

Similarly to the above-described example of FIG. 18A, the user may control the exposure parameters, the operation of the image processor 120, and the like by manipulating the input device 132.

When performing angiography, the X-ray imaging apparatus 100 may have the structure of C-arm as shown in FIG. 18C. The X-ray source 111 and the X-ray detector 112 may be mounted in both ends of a C-shaped arm (or C-arm) 107, respectively. The C-arm 107 may be connected to the gantry 105 through a connection shaft 109, and rotated in an orbital direction.

When a patient table 108 is located between the X-ray source 111 and the X-ray detector 112 and an object is located on the patient table, the X-ray source 111 irradiates the object with X-rays, and the X-ray detector 112 detects the irradiated X-rays to acquire an X-ray image of the object. In this instance, the acquired X-ray image may be moving images, and the display 131 may display the X-ray moving images in real-time.

In the case in which the X-ray moving images are generated, the object is exposed for a long period of time, and therefore it is important to irradiate the object with low-dose X-rays. The X-ray imaging apparatus 100 according to an exemplary embodiment performs material separation and scattering correction in the cyclic iterative manner, and therefore it is possible accurately separate blood vessels, surgical tools, and the like even in a low-dose X-ray environment.

For example, when performing a surgical procedure of inserting a stent into the blood vessel by using the X-ray imaging apparatus 10, a user may perform the surgical procedure while viewing a stent separation image or a blood vessel separation image displayed on the display 131. In this instance, a plurality of displays 131 may be provided in the X-ray imaging apparatus 100 to display an image for each display 131, or a single display 131 may be divided into a plurality of regions so that an image for each of the divided regions may be displayed.

Hereinafter, an image processing apparatus according to an exemplary embodiment that performs material separation and scattering correction in the cyclic iterative manner, by using the multi-energy X-ray image transmitted from an external device will be described.

Figure 19:
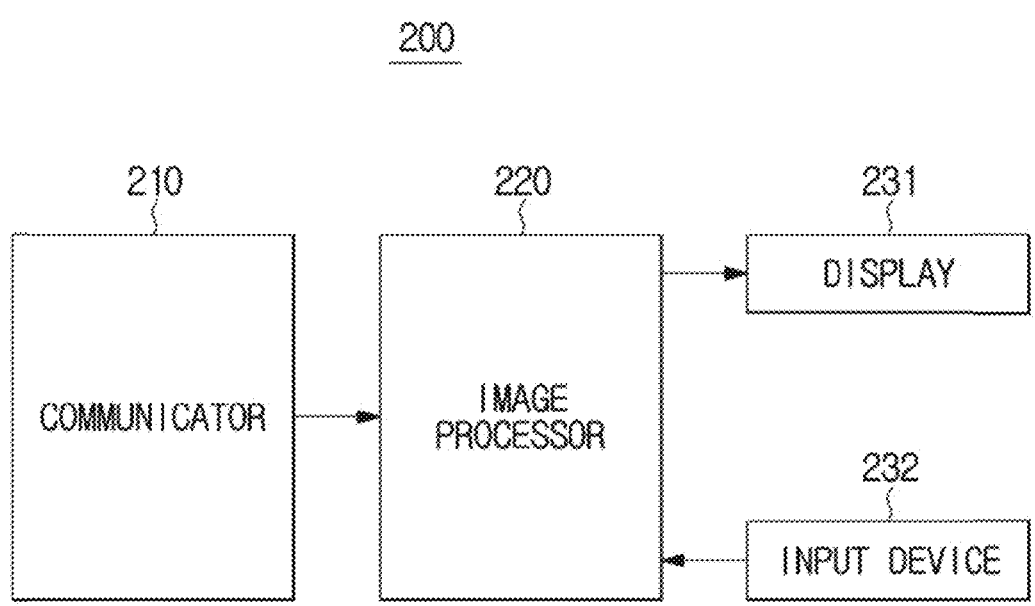
FIG. 19 is a control block diagram illustrating an image processing apparatus according to an exemplary embodiment.
Figure 20:
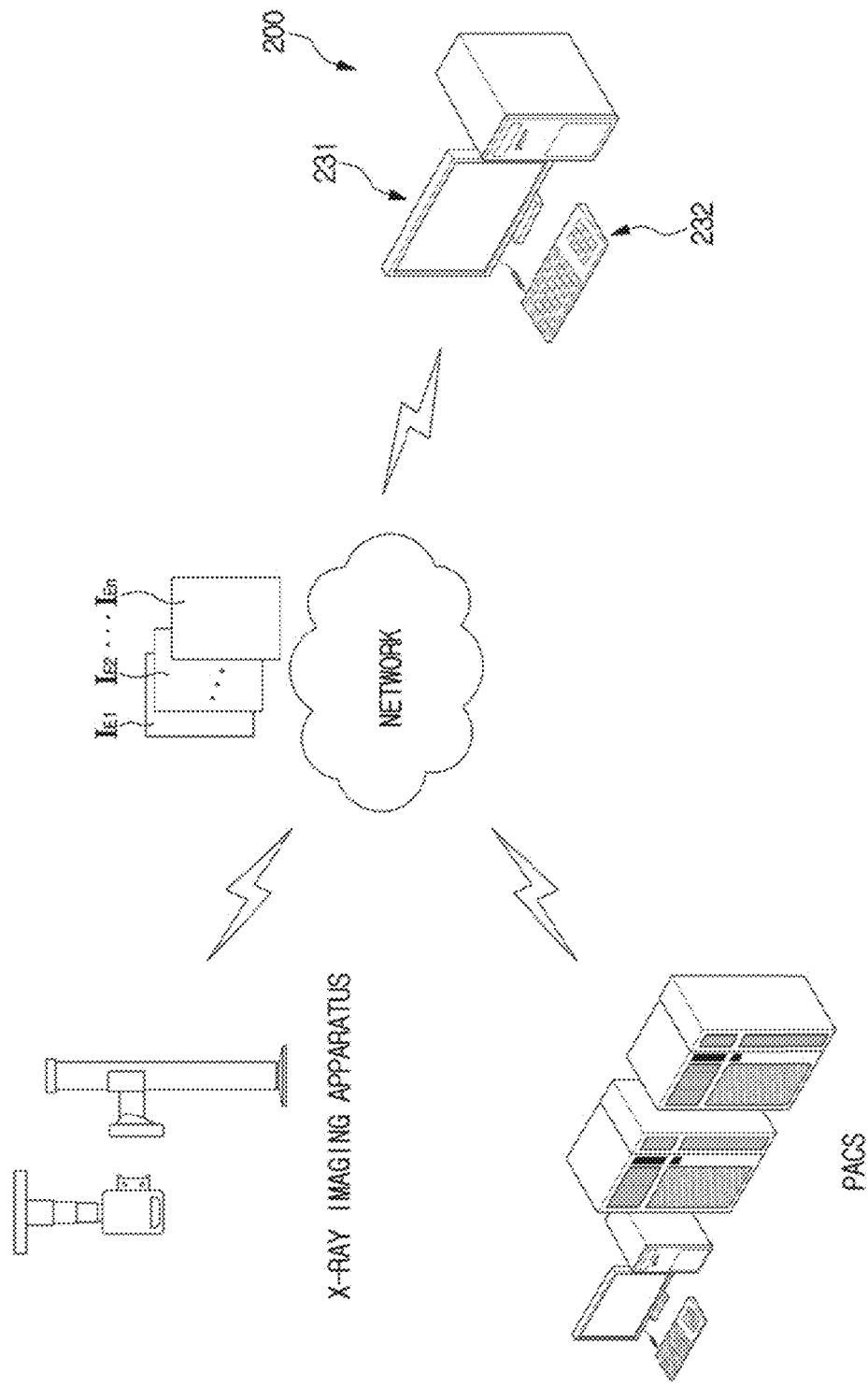
FIG. 20 is an appearance diagram of an image processing apparatus according to an exemplary embodiment.

FIG. 19 is a control block diagram illustrating an image processing apparatus according to an exemplary embodiment, and FIG. 20 is a diagram of an image processing apparatus according to an exemplary embodiment.

Referring to FIG. 19, an image processing apparatus 200 according to an exemplary embodiment includes a communicator 210 that receives a multi-energy X-ray image, an image processor 220 that performs material separation and scattering correction on materials shown in the corresponding image by using the multi-energy X-ray image, a display 231 that provides a material separation result to a user, and an input device 232 that receives control commands for operations of the image processing apparatus from the user.

The image processing apparatus 200 may be a computer that is used by a user such as radiographers. A multi-energy X-ray image may be imaged through the X-ray imaging apparatus 100, and then the imaged multi-energy X-ray image may be transmitted to the image processing apparatus 200. Alternatively, the imaged multi-energy X-ray image may be transmitted through a picture archiving communication system (PACS) that stores and transmits medical images acquired from a plurality of medical imaging apparatuses 100.

Referring to FIG. 19 and FIG. 20, the communicator 210 may receive multi-energy X-ray images $I_{E1}$ to $I_{En}$ from the X-ray imaging apparatus 100 or the PACS through a network. The network may include wired or wireless Internet, a wired public network, a wireless mobile communication network, a core network integrated with the portable Internet, or an open computer network that provides a variety of services existing in a transmission control protocol/internet protocol (TCP/IP) protocol and the higher layer, for example, a hypertext transfer protocol (HTTP), telnet, a file transfer protocol (FTP), a domain name system (DNS), a simple mail transfer protocol (SMTP), and the like.

In addition, the image processing apparatus 200 may be included in the PACS. In this case, the communicator 210 may receive the multi-energy X-ray image from the X-ray imaging apparatus 100 through the network.

In addition, the image processing apparatus 200 may be included in the X-ray imaging apparatus 100. In this case, the image processing apparatus 200 may be provided in the workstation of the X-ray imaging apparatus 100, and the communicator 210 may receive the multi-energy X-ray image from the X-ray detector 112.

The multi-energy X-ray image received by the communicator 210 may be an image on which preprocessing such as gain correction, offset correction, or the like has been performed, or a raw image on which preprocessing. Has not been performed.

The image processor 220 performs material separation and scattering correction in the cyclic iterative manner, by using the multi-energy X-ray image received by the communicator 210. In this instance, when the received multi-energy X-ray image is the raw image on which preprocessing has not been performed, the image processor 220 may perform preprocessing such as gain correction, offset correction, or the like, and then perform material separation.

The descriptions of material separation and scattering correction performed by the image processor 220 are the same as those of the image processor 120 of the above-described X-ray imaging apparatus 100, and thus will be here omitted.

The image processor 220 may generate an image for providing the material separation result to the user. For example, the image processor 220 may perform postprocessing on the material separation image to which the final thickness of each material is applied, or generate the highlighted material image by applying weighted subtraction to the multi-energy X-ray image and combine the generated highlighted material image and final thickness information of each material.

The operation of the image processor 220 may be controlled according to a user's command input through the input device 232. The user may select one of the material separation image and the highlighted material image, or select whether the separated material information and the highlighted material image are to be combined.

Alternatively, the operation of the image processor 220 may be automatically controlled by the image processing apparatus 200. Although not shown, the image processing apparatus 2 may further include a controller that controls the image processor 220. Here, the controller may select one of the material separation image and the highlighted material image based on at least one of the imaging parameters of the X-ray image, or select whether the separated material information and the highlighted material image are to be combined. Description of the controller is the same as that in FIG. 12 which has been described above.

Hereinafter, an X-ray image generation method according to an exemplary embodiment will be described. When performing the X-ray image generation method according to an exemplary embodiment, the above-described X-ray imaging apparatus 100 or image processing apparatus 200 may be used.

Figure 21:
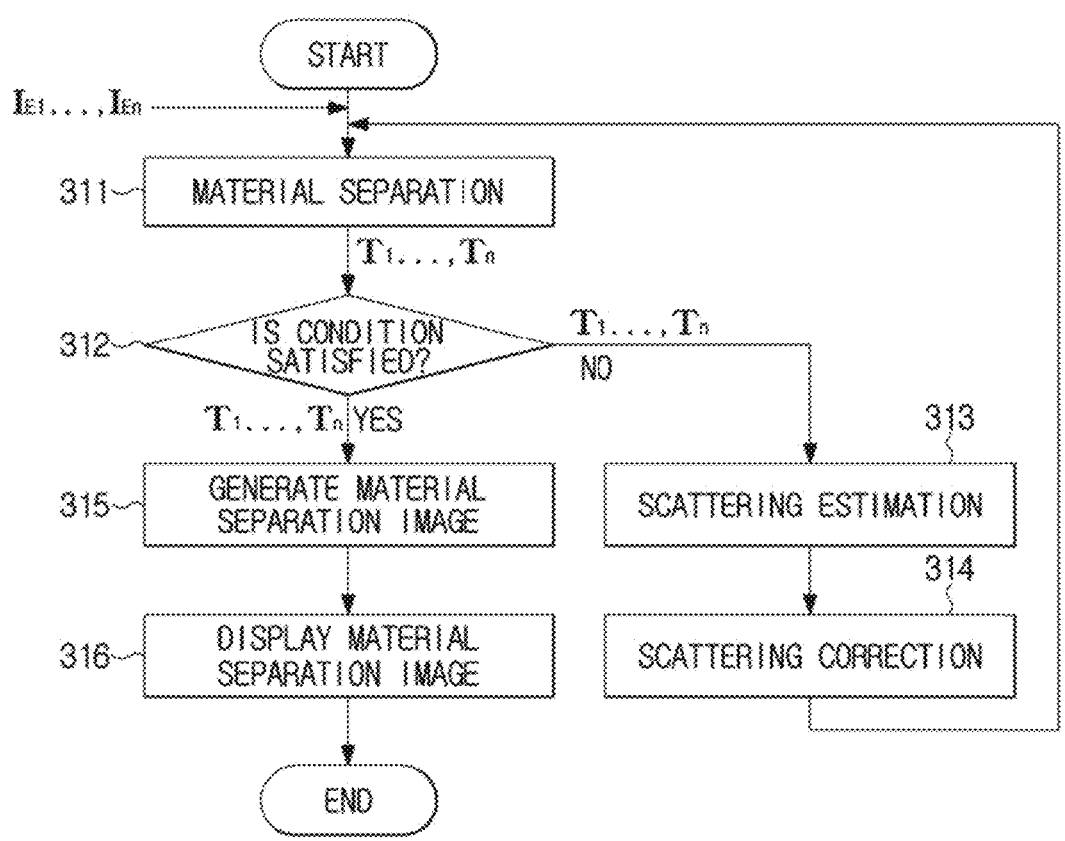
FIGS. 21 and 22 are flowcharts of an image processing method according to exemplary embodiments.
Figure 22:
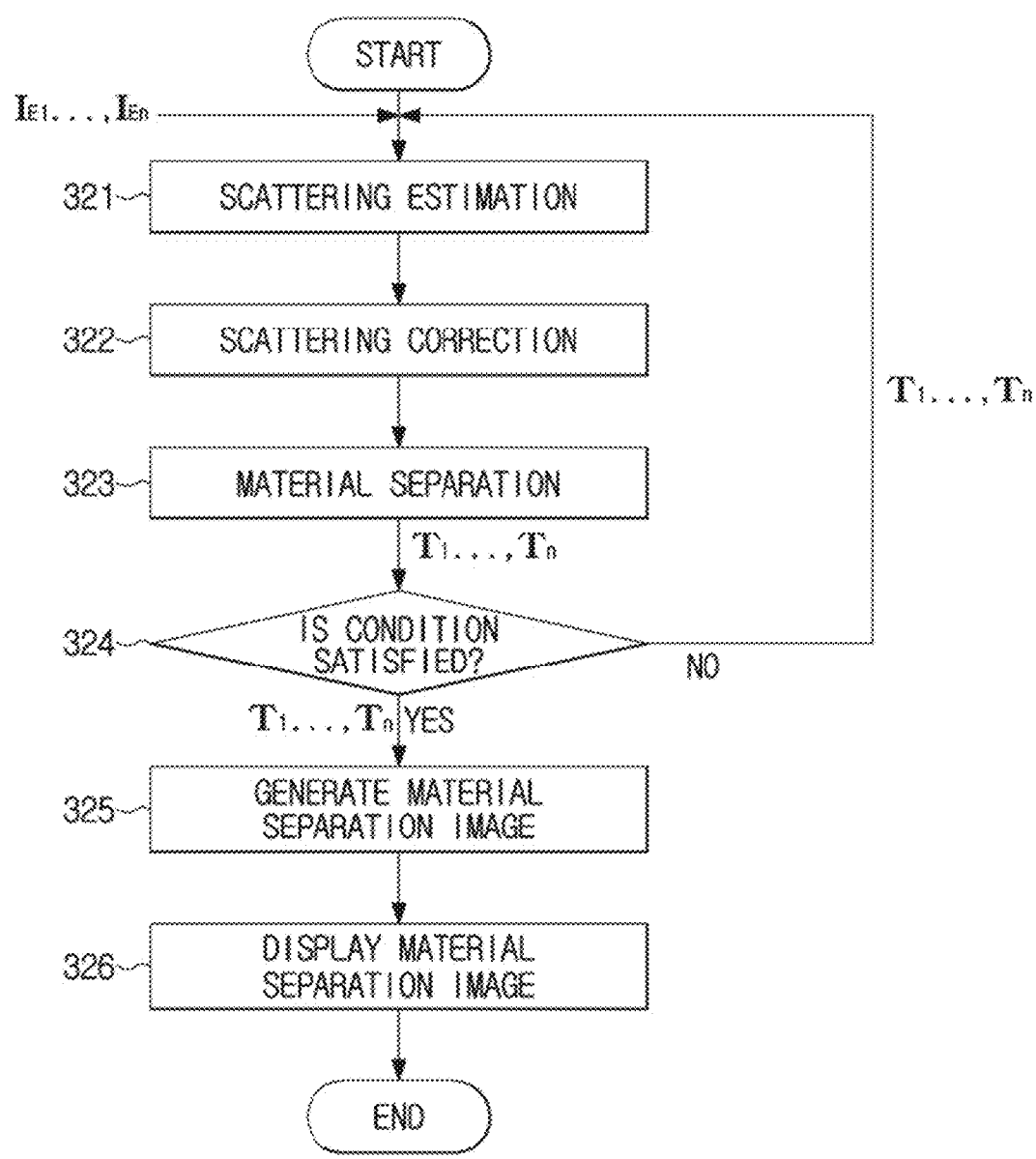

FIGS. 21 and 22 are flowcharts of an image processing method according to exemplary embodiments.

Referring to FIG. 21, in operation 311, when the multi-energy X-ray images $I_{E1}$ to $I_{En}$ are input, material separation is performed by using the input multi-energy X-ray images $I_{E1}$ to $I_{En}$.

The input multi-energy X-ray images $I_{E1}$ to $I_{En}$ may be images on which preprocessing such as gain correction or offset correction has been performed, or raw images on which preprocessing has not been performed. When the multi-energy X-ray image is the raw image on which preprocessing has not been performed, the preprocessing may be performed, and then material separation may be performed.

Material separation may be performed by calculating a thickness of a material. The thickness of each material may be calculated by using at least one of detection sensitivity of X-rays for each energy band, an attenuation coefficient of each material, and incident intensity of X-rays. In this instance, it is possible to perform material separation without performing scattering correction, by using the above-described Equation 1 to Equation 4, or perform material separation together with scattering correction by using Equation 6.

In operation 315, when the material separation result satisfies a predetermined verification condition (YES in operation 312), a material separation image is generated. In operation 316, the generated material separation image is displayed in operation 316. Here, postprocessing may be performed on the material separation image to which the final thickness of each material is applied, and the corresponding image may be displayed. Alternatively, a highlighted material image for each material may be generated by applying weighted subtraction to the multi-energy X-ray image, and the generated highlighted material image and final thickness information of each material may be combined to be displayed.

Here, the predetermined verification condition may be used to determine to ensure the reliability of the material separation result. For example, whether a difference between calculated data and measured data is included in a predetermined error range may be set as the verification condition. Specifically, when a difference between X-ray intensity calculated by considering the acquired thickness $T_i$ for each material and actually detected X-ray intensity is included in a predetermined error range, the method may stop performing scattering correction and material separation, and otherwise, continue to perform scattering correction and material separation.

As another example, whether a cost function is defined, and the defined cost function is minimized may be set as the verification condition. The cost function may be defined by using the intensity of detected X-rays, a calculated thickness for each material, an effective absorption coefficient based on polychromatic X-rays, or the like. In this instance, the effective absorption coefficient may be obtained by considering a difference between an absorption coefficient for each material in an actual polychromatic X-ray environment and a theoretical absorption coefficient in a monochromatic X-ray environment, and measured through an appropriately designed phantom experiment.

When the material separation result does not satisfy the predetermined verification condition (NO in operation 312), scattering estimation of operation 313 and scattering correction of operation 314 are performed, and material separation is performed again. X-ray scattering may be estimated by using the calculated thickness of each material. For example, it is possible to estimate X-ray scattering through simulation that uses, as factors, a thickness of a material, a scattering vector, a length of a scattering path, a location of the X-ray detector, response characteristics of the X-ray detector, and the like. Next, scattering correction is performed by using the estimated X-ray scattering. Scattering correction may refer to removing X-ray scattering from the X-ray image. Next, material separation is performed again by using the multi-energy X-ray image on which scattering correction has been performed, and the above process is repeatedly performed until the predetermined verification condition is satisfied.

Alternatively, scattering estimation and scattering correction may be first performed, and then material separation may be performed. Referring to FIG. 22, when the multi-energy X-ray images $I_{E1}$ to $I_{En}$ are input, scattering estimation of operation 321 and scattering correction of operation 322 are first performed on the input multi-energy X-ray image. Initial scattering estimation before performing material separation may be performed by using, for example, boundary detection of the multi-energy X-ray image and standard tissue composition that is given in advance.

Next, material information may be acquired by performing material separation of operation 323 by using the multi-energy X-ray image on which scattering correction has been performed. For example, by using the above-described Equation 4 and Equation 6, thicknesses $T_1$ to $T_n$ of individual materials may be calculated.

In operation 325, when the material separation result satisfies the predetermined verification condition (YES in operation 324), a material separation image is generated. In operation 326, the generated material separation image is displayed. Descriptions of a process of determining whether the predetermined verification condition is satisfied and a process of generating and displaying the material separation image are the same as those in operations 312, 315, and 316 of FIG. 21.

When the material separation result does not satisfy the predetermined verification condition (NO in operation 324), scattering estimation and scattering correction are performed by using the acquired material information. Here, scattering estimation may be performed through simulation that uses, as factors, a thickness of a material, a scattering vector, a length of a scattering path, a location of the X-ray detector, response characteristics of the X-ray detector, and the like. Next, scattering correction is performed by using the estimated X-ray scattering. Next, material separation is performed by using the multi-energy X-ray image on which scattering correction has been performed, and the above process is repeatedly performed until the predetermined verification condition is satisfied.

As described above, according to the X-ray imaging apparatus, the image processing apparatus, and the X-ray image generation method according to the exemplary embodiments can perform material separation and/or scattering correction by using the multi-energy X-ray image in the cyclic iterative manner, thereby improving the accuracy of material separation and/or scattering correction.

In addition, according to the exemplary embodiments, when performing material separation and scattering correction in the cyclic iterative manner, distinction among materials can be improved even in a low-dose X-ray environment, and thereby can reduce X-ray exposure of a patient and be effectively applied even to an X-ray moving image field.

The image processing methods according to the exemplary embodiments may be recorded as programs that can be executed on a computer and implemented through general-purpose digital computers which can run the programs using a computer-readable recording medium. Data structures described in the above methods can also be recorded on a computer-readable recording medium in various manners. Examples of the computer-readable recording medium include storage media such as magnetic storage media (e.g., read-only memories (ROMs), floppy disks, hard disks, etc.) and optical recording media (e.g., CD-ROMs or DVDs). Furthermore, the computer-readable recording media may include computer storage media and communication media. The computer storage media may include both volatile and nonvolatile and both detachable and non-detachable media implemented by any method or technique for storing information such as computer-readable instructions, data structures, program modules or other data. The communication media may store computer-readable instructions, data structure, program modules, other data of a modulated data signal such as a carrier wave, or other transmission mechanism, and may include any information transmission media.

Although a few embodiments have been shown and described, it would be appreciated by those skilled in the art that changes may be made in these exemplary embodiments without departing from the principles and spirit of the disclosure, the scope of which is defined in the claims and their equivalents.

What is claimed is:

1. An X-ray imaging apparatus comprising:
    an image capturing device configured to acquire a plurality of X-ray images of an object in different energy bands;
    an image processor configured to perform scattering correction on the plurality of X-ray images to remove X-ray scattering from the plurality of X-ray images, perform material separation on the plurality of X-ray images on which the scattering correction has been performed to acquire material information of at least one material included in the object, and repeatedly perform the scattering correction and the material separation depending on whether a predetermined condition is satisfied; and
    a display configured to display at least one selected based on a result of comparison between a dose of X-rays applied to acquire the plurality of X-ray images and a predetermined reference dose, from among a highlighted material image generated by applying weighted subtraction to the plurality of X-ray images and a material separation image generated by performing the material separation.

2. The X-ray imaging apparatus according to claim 1, wherein, when the predetermined condition is not satisfied, the image processor is configured to repeatedly perform the scattering correction on the plurality of X-ray images by using the acquired material information, and repeatedly perform the material separation on the plurality of X-ray images on which the scattering correction has been performed.

3. The X-ray imaging apparatus according to claim 1, wherein, when the predetermined condition is not satisfied, the image processor is configured to estimate the X-ray scattering in the plurality of X-ray images by using the material information.

4. The X-ray imaging apparatus according to claim 3, wherein the image processor is configured to perform the scattering correction by removing the estimated X-ray scattering from the plurality of X-ray images.

5. The X-ray imaging apparatus according to claim 1, wherein the material information comprises a thickness of a material of the object in a field of view (FOV) of the plurality of X-ray images.

6. The X-ray imaging apparatus according to claim 1, wherein the predetermined condition comprises whether a difference between X-ray intensity calculated based on the acquired material information and measured X-ray intensity is within a predetermined error range.

7. The X-ray imaging apparatus according to claim 1, wherein the predetermined condition comprises whether a cost function defined by using the acquired material information is minimized.

8. The X-ray imaging apparatus according to claim 1, wherein the display is configured to provide the acquired material information to a user.

9. The X-ray imaging apparatus according to claim 8, wherein the display is configured to display the material separation image.

10. The X-ray imaging apparatus according to claim 8, wherein the display is configured to display an image obtained by combining the acquired material information and the highlighted material image.

11. The X-ray imaging apparatus according to claim 1, further comprising:
an input device configured to receive a selection of at least one from among the highlighted material image and the material separation image,
wherein the display is further configured to display the at least one from among the highlighted material image and the material separation image according to the selection received by the input device.

12. The X-ray imaging apparatus according to claim 11, wherein the display is configured to display an image obtained by combining the highlighted material image and the material separation image, according to the selection received by the input device.

13. The X-ray imaging apparatus according to claim 1, further comprising:
a controller configured to select at least one from among the highlighted material image and the material separation image, based on imaging parameters of the plurality of X-ray images other than the dose of X-rays.

14. The X-ray imaging apparatus according to claim 13, wherein the controller is further configured to control the display to display an image obtained by combining the highlighted material image and the material separation image, according to a selection by the controller.

15. An X-ray imaging apparatus comprising:
an image capturing device configured to acquire a plurality of X-ray images of an object in different energy bands; and
an image processor configured to perform material separation on the plurality of X-ray images to acquire material information of at least one material included in the object, repeatedly perform scattering correction by using the acquired material information to remove X-ray scattering from the plurality of X-ray images and the material separation on the plurality of X-ray images on which the scattering correction has been performed, depending on whether a predetermined condition is satisfied; and
a display configured to display at least one selected based on a result of comparison between a dose of X-rays applied to acquire the plurality of X-ray images and a predetermined reference dose, from among a highlighted material image generated by applying weighted subtraction to the plurality of X-ray images and a material separation image generated by performing the material separation.

16. The X-ray imaging apparatus according to claim 15, wherein, when the predetermined condition is not satisfied, the image processor is configured to repeatedly perform the scattering correction on the plurality of X-ray images by using the acquired material information, and repeatedly perform the material separation on the plurality of X-ray images on which the scattering correction has been performed.

17. The X-ray imaging apparatus according to claim 15, wherein the image processor is configured to perform a first material separation without performing the scattering correction or after performing the scattering correction by using an initial scattering estimation value.

18. The X-ray imaging apparatus according to claim 15, wherein the display is configured to provide the acquired material information to a user.

19. An image processing apparatus comprising:
a communicator, implemented by a computer, configured to receive a plurality of X-ray images of an object in different energy bands; and
an image processor configured to perform scattering correction on the plurality of X-ray images to remove X-ray scattering from the plurality of X-ray images, perform material separation on the plurality of X-ray images on which the scattering correction has been performed to acquire material information of at least one material included in the object, and repeatedly perform the scattering correction and the material separation depending on whether a predetermined condition is satisfied; and
a display configured to display at least one selected based on a result of comparison between a dose of X-rays applied to acquire the plurality of X-ray images and a predetermined reference dose, from among a highlighted material image generated by applying weighted subtraction to the plurality of X-ray images and a material separation image generated by performing the material separation.

20. The image processing apparatus according to claim 19, wherein, when the predetermined condition is not satisfied, the image processor is configured to repeatedly perform the scattering correction on the plurality of X-ray images by using the acquired material information, and repeatedly perform the material separation on the plurality of X-ray images on which the scattering correction has been performed.

21. The image processing apparatus according to claim 19, wherein, when the predetermined condition is not satisfied, the image processor is configured to estimate the X-ray scattering in the plurality of X-ray images by using the material information, and perform the scattering correction by removing the estimated X-ray scattering from the plurality of X-ray images.

22. The image processing apparatus according to claim 19, wherein the material information comprises a thickness of a material of the object in a field of view (FOV) of the plurality of X-ray images.

23. The image processing apparatus according to claim 19, further comprising:
an input device configured to receive a selection of at least one from among the highlighted material image and the material separation image.

24. The image processing apparatus according to claim 19,
wherein the display is configured to provide the acquired material information to a user.

25. An image processing apparatus comprising:
a communicator, implemented by a computer, configured to receive a plurality of X-ray images of an object in different energy bands;
an image processor configured to perform material separation on the plurality of X-ray images to acquire material information of at least one material included in the object, and repeatedly perform scattering correction by using the acquired material information to remove X-ray scattering from the plurality of X-ray images and the material separation on the plurality of X-ray images on which the scattering correction has been performed, depending on whether a predetermined condition is satisfied;

a display configured to provide the acquired material information to a user; and a controller configured to, based on a result of comparison between a dose of X-rays applied to acquire the plurality of X-ray images and a predetermined reference dose, control the display to display at least one from among a highlighted material image, generated by applying weighted subtraction to the plurality of X-ray images, and a material separation image generated by performing the material separation.

26. The image processing apparatus according to claim 25, wherein the image processor is configured to repeatedly perform the scattering correction on the plurality of X-ray images by using the acquired material information and perform the material separation on the plurality of X-ray images on which the scattering correction has been performed when the predetermined condition is not satisfied.

27. The image processing apparatus according to claim 25, wherein the image processor is configured to perform a first material separation without performing the scattering correction or after performing the scattering correction by using an initial scattering estimation value.

28. The image processing apparatus according to claim 25, wherein the predetermined condition comprises whether a difference between X-ray intensity calculated based on the acquired material information and measured X-ray intensity is within a predetermined error range.

29. An image processing method comprising:
performing scattering correction on a plurality of X-ray images of an object in different energy bands to remove X-ray scattering from the plurality of X-ray images;
performing material separation on the plurality of X-ray images on which the scattering correction has been performed to acquire material information of at least one material included in the object;
repeatedly performing the scattering correction and the material separation depending on whether a predetermined condition is satisfied; and
selecting at least one from among a highlighted material image, generated by applying weighted subtraction to the plurality of X-ray images, and a material separation image generated by performing the material separation, the selecting being based on a result of comparison between a dose of X-rays applied to acquire the plurality of X-ray images and a predetermined reference dose.

30. The image processing method according to claim 29, wherein the repeatedly performing comprises, when the predetermined condition is not satisfied, repeatedly performing the scattering correction on the plurality of X-ray images by using the acquired material information, and repeatedly performing the material separation on the plurality of X-ray images on which the scattering correction has been performed.

31. The image processing method according to claim 29, further comprising:
providing the acquired material information to a user when the predetermined condition is satisfied.

32. An image processing method comprising:
performing material separation on a plurality of X-ray images of an object in different energy bands to acquire material information of at least one material included in the object;
repeatedly performing scattering correction by using the acquired material information to remove X-ray scattering from the plurality of X-ray images, and the material separation by using the plurality of X-ray images on which the scattering correction has been performed, depending on whether a predetermined condition is satisfied; and
selecting at least one from among a highlighted material image generated by applying weighted subtraction to the plurality of X-ray images and a material separation image generated by performing the material separation, the selecting being based on a result of comparison between a dose of X-rays applied to acquire the plurality of X-ray images and a predetermined reference dose.

33. The image processing method according to claim 32, wherein the repeatedly performing comprises, when the predetermined condition is not satisfied, repeatedly performing the scattering correction on the plurality of X-ray images by using the acquired material information, and repeatedly performing the material separation on the plurality of X-ray images on which the scattering correction has been performed.

* * * * *